(12) United States Patent
Sokal et al.

(10) Patent No.: US 8,137,327 B2
(45) Date of Patent: Mar. 20, 2012

(54) VAGINAL DRUG DELIVERY SYSTEM AND METHOD

(75) Inventors: David C. Sokal, Durham, NC (US); Carol L. Joanis, Raleigh, NC (US); George A. M. Butterworth, Pittsboro, NC (US); James D. Reed, Raleigh, NC (US); Robert A. Johnson, Turnersville, NJ (US)

(73) Assignee: Family Health International, Durham, NC (US)

( * ) Notice: Subject to any disclaimer, the term of this patent is extended or adjusted under 35 U.S.C. 154(b) by 250 days.

(21) Appl. No.: 11/454,604

(22) Filed: Jun. 16, 2006

(65) Prior Publication Data

US 2007/0293837 A1    Dec. 20, 2007

(51) Int. Cl.
*A61M 31/00* (2006.01)
*A61F 13/15* (2006.01)
*A61F 13/20* (2006.01)
*A61F 6/06* (2006.01)

(52) U.S. Cl. ........ 604/286; 604/285; 604/358; 604/367; 128/830; 128/834

(58) Field of Classification Search ............. 604/385.18, 604/286, 285; 424/430; 128/834, 835, 838, 128/841
See application file for complete search history.

(56) References Cited

U.S. PATENT DOCUMENTS

| | | | |
|---|---|---|---|
| 3,393,678 A | 7/1968 | Pacini | |
| 3,762,414 A | 10/1973 | Burnhill | |
| 3,805,785 A * | 4/1974 | Marginet | 604/12 |
| 3,881,485 A * | 5/1975 | Davis, Jr. | 604/286 |
| 3,902,493 A * | 9/1975 | Baier et al. | 604/286 |
| 3,916,898 A * | 11/1975 | Robinson | 604/515 |
| 3,918,452 A | 11/1975 | Cornfeld | |
| 3,921,636 A | 11/1975 | Zaffaroni | |
| 3,993,073 A | 11/1976 | Zaffaroni | |
| 4,027,673 A | 6/1977 | Poncy et al. | |
| 4,106,154 A | 8/1978 | Forsberg | |
| 4,108,180 A * | 8/1978 | Moehrle | 604/369 |
| 4,228,797 A | 10/1980 | Dickey | |
| 4,246,896 A | 1/1981 | Horne, Jr. et al. | |

(Continued)

FOREIGN PATENT DOCUMENTS

EP    0 679 379 A1    2/1995

(Continued)

OTHER PUBLICATIONS

PCT International Search Report, Jan. 8, 2008, pp. 1-3, US Patent and Trademark Office, Commissioner of Patents, Alexandria, Virginia, US.

(Continued)

*Primary Examiner* — Tatyana Zalukaeva
*Assistant Examiner* — Susan Su
(74) *Attorney, Agent, or Firm* — Womble Carlyle Sandridge & Rice, LLP

(57) ABSTRACT

A vaginal drug delivery system includes a device formed of porous material that holds a flowable therapeutic formulation. The device, preferably in a soft, prewetted state, is inserted into the vagina to reside typically at or near the cervix where it continuously releases the flowable therapeutic formulation through its outer surface which is in contact with the vaginal surfaces. In operation, the flowable therapeutic formulation migrates via capillary forces from a reservoir that is centrally located in the device and through a covering that envelopes the reservoir.

13 Claims, 14 Drawing Sheets

U.S. PATENT DOCUMENTS

| | | | |
|---|---|---|---|
| 4,286,596 A | | 9/1981 | Rubinstein |
| 4,309,997 A | | 1/1982 | Donald |
| 4,320,759 A | | 3/1982 | Theeuwes |
| 4,340,055 A | | 7/1982 | Sneider |
| 4,553,965 A | | 11/1985 | Conn et al. |
| 4,576,604 A | | 3/1986 | Guittard et al. |
| 4,582,717 A | | 4/1986 | Von Bittera et al. |
| 4,663,148 A | * | 5/1987 | Eckenhoff et al. ............ 424/454 |
| 4,692,143 A | * | 9/1987 | Gero ............................ 604/515 |
| 4,693,705 A | * | 9/1987 | Gero .............................. 604/48 |
| 4,786,500 A | | 11/1988 | Wong |
| 4,858,624 A | | 8/1989 | Shihata |
| 5,000,749 A | | 3/1991 | LeVeen et al. |
| 5,105,827 A | * | 4/1992 | Augros ........................ 128/832 |
| 5,201,326 A | | 4/1993 | Kubicki et al. |
| 5,231,992 A | * | 8/1993 | Leon ............................ 600/572 |
| 5,295,984 A | | 3/1994 | Contente et al. |
| 5,299,581 A | * | 4/1994 | Donnell et al. ............... 128/830 |
| 5,462,743 A | | 10/1995 | Turner et al. |
| 5,466,217 A | | 11/1995 | Myers et al. |
| 5,527,534 A | * | 6/1996 | Myhling ....................... 424/430 |
| 5,538,735 A | | 7/1996 | Ahn |
| 5,753,252 A | | 5/1998 | Brown-Skrobot |
| 5,819,742 A | | 10/1998 | Sokal et al. |
| 5,840,055 A | | 11/1998 | Sgro |
| 5,928,184 A | | 7/1999 | Etheredge et al. |
| 6,031,148 A | | 2/2000 | Hayes et al. |
| 6,074,630 A | * | 6/2000 | Devillez et al. ................. 424/59 |
| 6,086,909 A | * | 7/2000 | Harrison et al. .............. 424/430 |
| 6,096,332 A | | 8/2000 | Yang |
| 6,125,850 A | | 10/2000 | Sokal et al. |
| 6,155,259 A | | 12/2000 | Conte et al. |
| 6,186,994 B1 | | 2/2001 | Bowles et al. |
| 6,197,327 B1 | * | 3/2001 | Harrison et al. .............. 424/430 |
| 6,216,697 B1 | | 4/2001 | Moench et al. |
| 6,261,580 B1 | * | 7/2001 | Lehrter et al. ................. 424/402 |
| 6,303,697 B1 | | 10/2001 | Yuan et al. |
| 6,328,991 B1 | | 12/2001 | Myhling |
| 6,416,779 B1 | * | 7/2002 | D'Augustine et al. ........ 424/430 |
| 6,526,980 B1 | | 3/2003 | Tracy et al. |
| 6,558,362 B1 | | 5/2003 | Chaffringeon |
| 6,743,212 B1 | | 6/2004 | Cole et al. |
| 6,743,965 B2 | | 6/2004 | Yang et al. |
| 6,766,817 B2 | | 7/2004 | da Silva |
| 6,773,418 B1 | | 8/2004 | Sharrow et al. |
| 6,841,657 B2 | | 1/2005 | Eckert et al. |
| 6,861,520 B1 | | 3/2005 | Todd et al. |
| 6,899,700 B2 | * | 5/2005 | Gehling et al. ................ 604/285 |
| 6,918,404 B2 | | 7/2005 | Dias da Silva |
| 7,066,586 B2 | | 6/2006 | da Silva |
| 2001/0009993 A1 | | 7/2001 | Clifford |
| 2002/0107497 A1 | | 8/2002 | Osborn, III et al. |
| 2002/0161352 A1 | | 10/2002 | Lin et al. |
| 2002/0183216 A1 | | 12/2002 | Koenig et al. |
| 2003/0049302 A1 | | 3/2003 | Pauletti et al. |
| 2003/0120224 A1 | * | 6/2003 | Geiser et al. .................. 604/285 |
| 2003/0153864 A1 | | 8/2003 | Chaffringeon |
| 2003/0163103 A1 | | 8/2003 | Benita et al. |
| 2003/0191439 A1 | | 10/2003 | Chaffringeon |
| 2003/0191442 A1 | | 10/2003 | Bewick-Sonntag et al. |
| 2003/0203010 A1 | | 10/2003 | Wallo |
| 2004/0022861 A1 | | 2/2004 | Williams, III et al. |
| 2004/0155222 A1 | | 8/2004 | Kagawa et al. |
| 2004/0193124 A1 | | 9/2004 | Mizutani et al. |
| 2004/0225272 A1 | * | 11/2004 | Karapasha et al. ....... 604/385.17 |
| 2004/0260252 A1 | | 12/2004 | DiPiano et al. |
| 2005/0153123 A1 | | 7/2005 | Herfert et al. |
| 2005/0214251 A1 | | 9/2005 | Pohl et al. |
| 2005/0244365 A1 | | 11/2005 | Labib et al. |
| 2006/0034937 A1 | | 2/2006 | Patel |
| 2006/0106361 A1 | | 5/2006 | Muni et al. |
| 2007/0027425 A1 | * | 2/2007 | Osborn et al. ................... 604/16 |
| 2007/0043327 A1 | * | 2/2007 | Knox ............................. 604/286 |

FOREIGN PATENT DOCUMENTS

| | | |
|---|---|---|
| WO | 02 076426 A3 | 10/2002 |
| WO | WO03080019 A1 | 10/2003 |
| WO | WO03092653 A1 | 11/2003 |

OTHER PUBLICATIONS

Examination Report (UK Appln. No. GB0817324.7, issued Oct. 14, 2010); pp. 1-5.

UK Intellectual Property Office Combined Search and Examination Report (GB Appln. No. 1103494.9) Date of Report: Mar. 17, 2011, pp. 1-6.

* cited by examiner

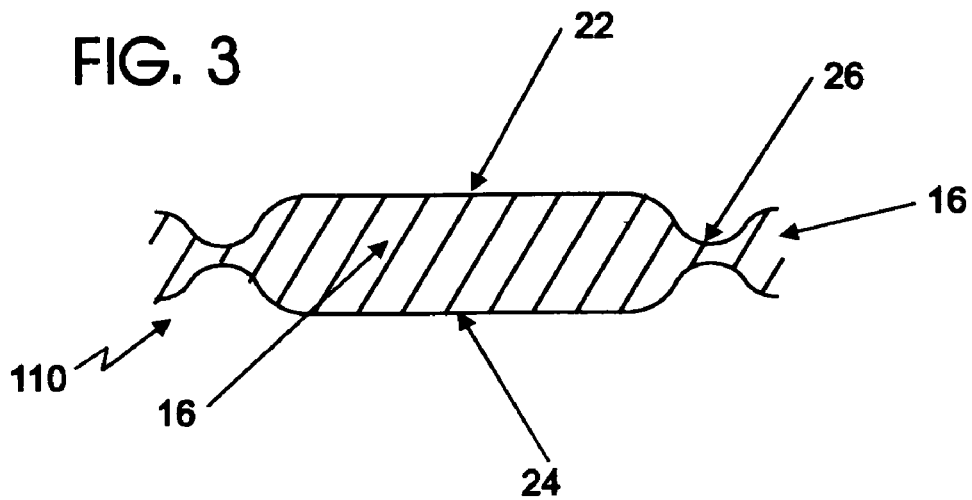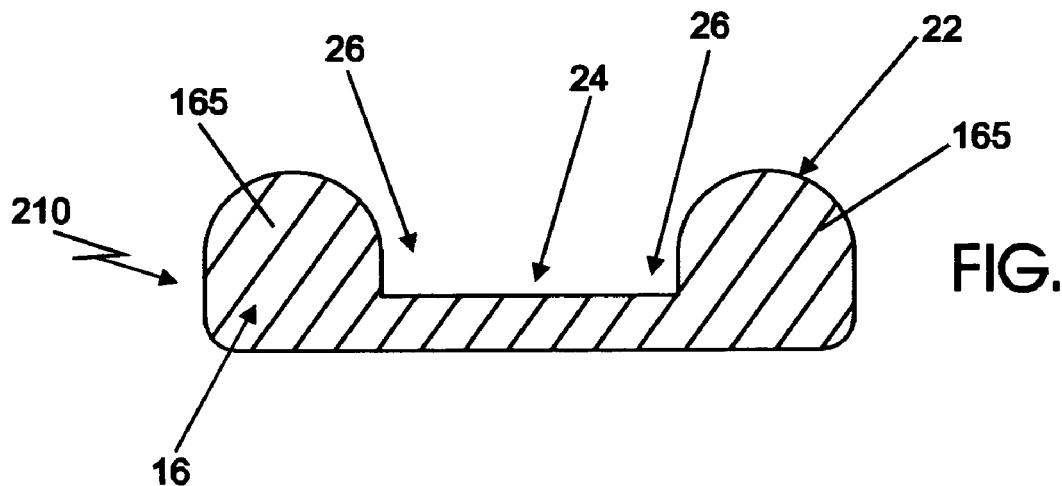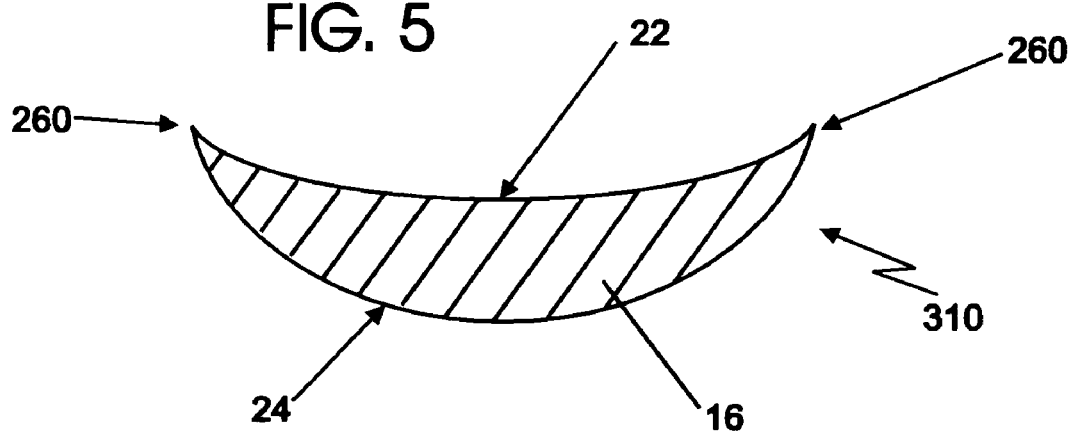

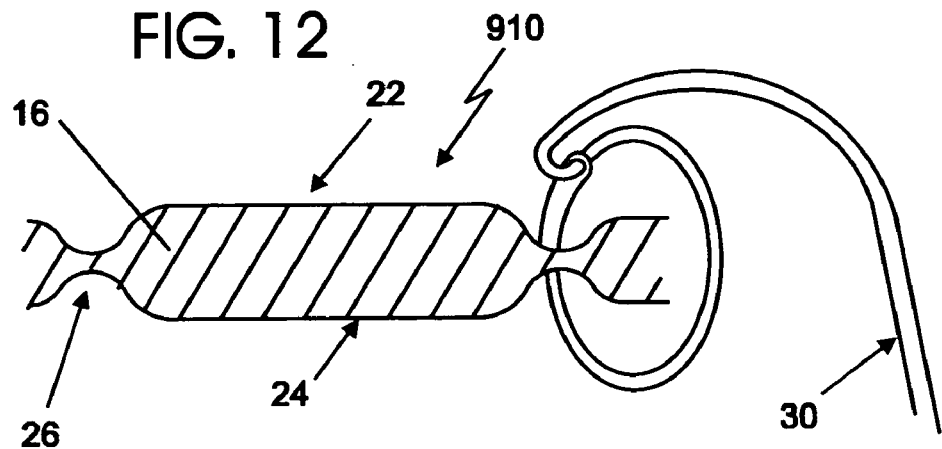
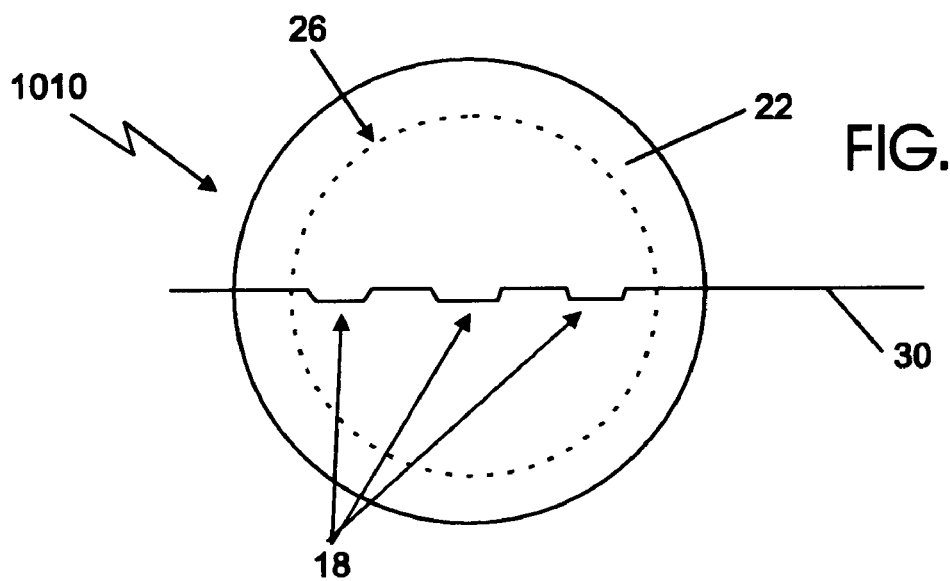
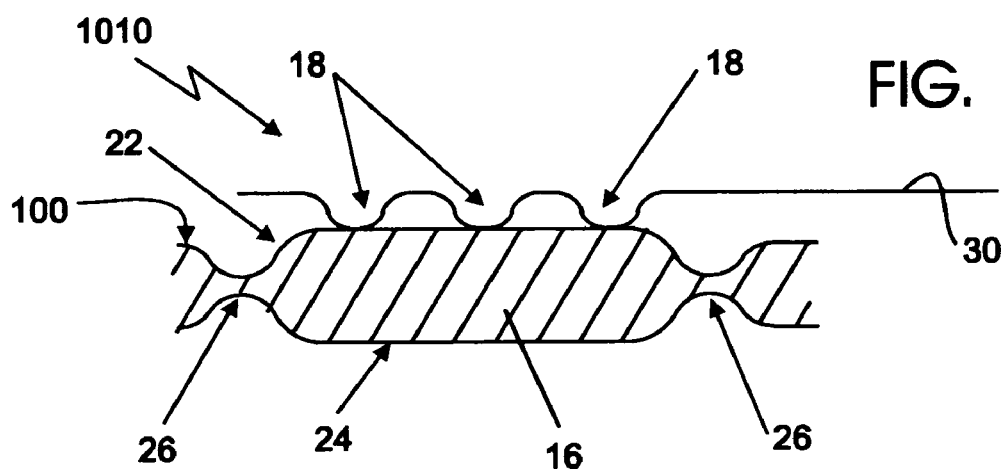

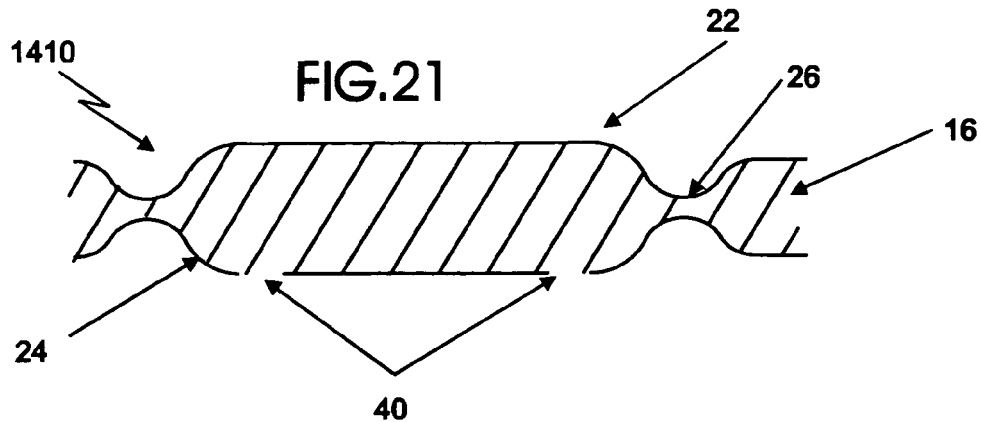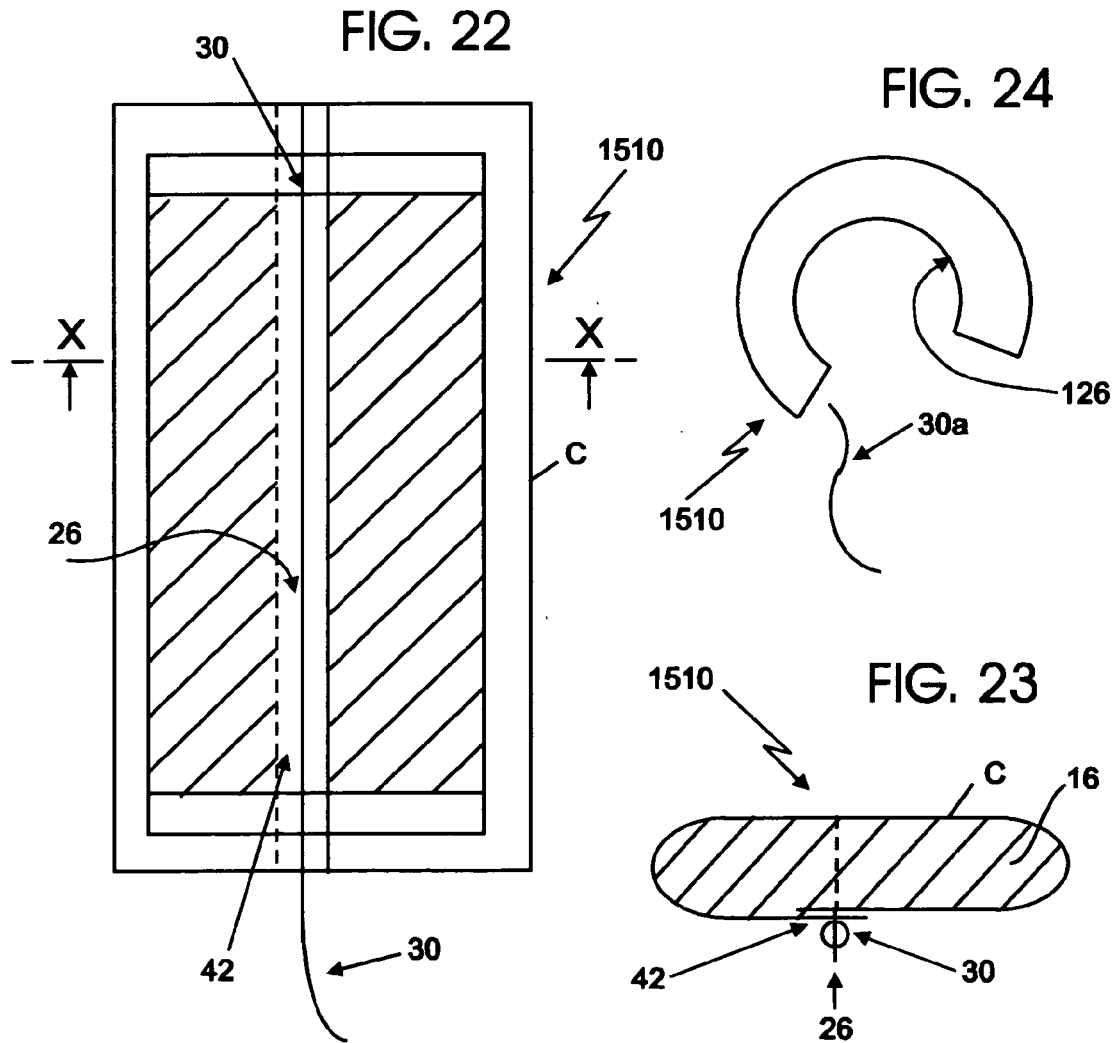

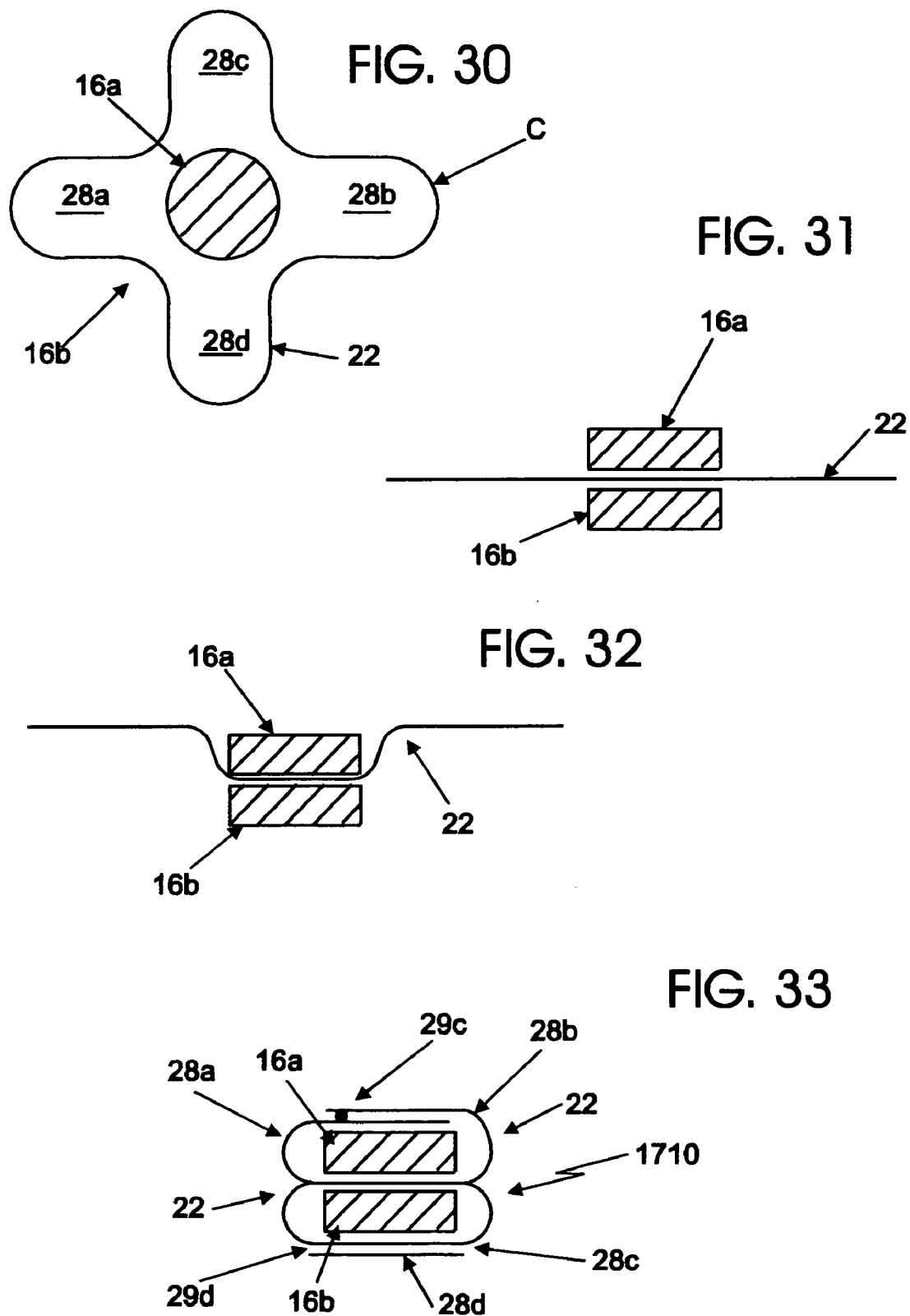

VAGINAL DRUG DELIVERY SYSTEM AND METHOD

GOVERNMENT LICENSE RIGHTS

The invention claimed herein was made under U.S. Agency for International Development, Cooperative Agreement #: CCP-A-00-95-00022-02, and the U.S. government has certain rights therein.

FIELD OF THE INVENTION

The invention relates to the delivery of therapeutic formulations to human females onto and sometimes through the vaginal surfaces. More particularly, the invention relates to drug delivery systems that include a device which is inserted into the vagina of a human female to reside typically at or near the cervix, and wherein the device contains and dispenses a flowable therapeutic formulation. The design of the device permits the delivery of therapeutic agents contained in the formulation onto the surrounding vaginal surfaces.

BACKGROUND OF THE INVENTION

Vaginal epithelial tissue has been shown to be receptive to drugs delivered by many different therapeutic formulations. However, there exists a problem of adequately and accurately targeting the delivery of these drugs, including therapeutic agents such as those used for contraception or for the prevention of infection by the human immunodeficiency virus (HIV) or by other sexually transmitted infections (STI). Additionally, it is difficult to maintain therapeutic agents in place on vaginal surfaces and replenish deleted areas with a fresh agent. Vaginal gels, foaming tablets, and creams are messy in application and prone to leakage. This problem is further complicated by the fact that an ideal location for topical therapeutic vaginal drug delivery is commonly at or near the woman's cervix. There exists a need for a convenient method that a woman can use that is safe and effective in keeping a delivered therapeutic formulation in the vagina at or near a desired target area for a specified/sufficient time period.

While it is known that every woman can theoretically locate and touch her cervix, many women have never done this and are not confident of their ability to place a diaphragm or cervical cap correctly over the cervix. Placement of gels, creams and foaming tables using a traditional applicator has additional limitations.

In addition to the conventional application of gels, foaming tablets, creams, diaphragms and cervical caps referred to above, prior attempts to deliver drugs via the vaginal surfaces have included tampon or tampon-like delivery systems. Some of these devices, for example, the devices of U.S. Pat. Nos. 5,201,326 and 6,086,909, are dry-absorbent tampons having external surfaces treated with dry materials that can be released when the tampon absorbs menses. One primary obstacle to the use of these devices is that the absorbent nature of these tampons makes it extremely difficult for the tampon to serve the dual purpose of delivering a therapeutic benefit while simultaneously absorbing menses. A therapeutic agent originally present on the dry surface of the tampon is likely to be carried into the body of the absorbent tampon rather than towards vaginal surfaces as the tampon absorbs menses. Consequently, the delivery of a therapeutic agent by this method is unpredictable, generally requiring a large dose of the agent on the tampon surface. This is undesirable from both economic and safety standpoints.

Other tampon-like drug delivery systems, for example, those shown in U.S. Pat. Nos. 3,921,636; 3,933,073 and U.S. Application 2003/0163103, utilize absorbent tampons that deliver drugs at controlled rates to the vagina via microdiffusion. These devices store drugs in microcapsules or within a permeable membrane for controlled release into the vagina, which is triggered by body heat or moisture. The microdiffusion approach is problematic because it deals with the controlled release of very small quantities of a drug from an essentially dry tampon and programmed by the diffusive nature of the microporous materials containing the drug. The rate of diffusion cannot be increased or decreased according to an instantaneous need from the surrounding vaginal tissue. Another U.S. Pat. No. 3,921,636, specifies that the drug be in non-crushable media to avoid device damage before use, but this can create discomfort when the product is worn.

Another class of devices includes those described in U.S. Pat. Nos. 4,320,759; 4,576,604; and 4,786,500 wherein tampon-like drug delivery devices deliver therapeutic formulations to the vaginal walls via osmosis. A principal drawback of these devices is that they deliver small quantities of concentrated drugs at a very slow rate and could never be expected to provide the quantities of a beneficial, therapeutic agent which could quickly coat the vaginal surfaces with, for example, a spermicidal formulation for prevention of pregnancy. For such a purpose, the device might be inserted only a few minutes prior to sexual intercourse and rapid delivery of the therapeutic agent would be required.

Attempts have been made to develop tampons as drug delivery systems by incorporating small quantities of a concentrated therapeutic agent on and/or within a dry-compressed tampon. Unfortunately, if it is used intra-menstrually (i.e., when there is no menstrual flow), there is insufficient vaginal wetness to cause the tampon to expand. Furthermore, it is risky and medically unacceptable to insert a dry tampon when a woman is not menstruating, as it can predispose the woman to irritation, discomfort, epithelial tearing, and possibly to toxic shock syndrome. Under normal menstrual conditions, the insertion of a dry, compressed tampon results in its expansion by wetting with menses. As it absorbs menses, any incorporated therapeutic agent dissolves in the surrounding vaginal tissue (U.S. Pat. No. 5,201,326). Unfortunately, the concentration of the therapeutic agent delivered varies both between and within individual tampon insertions due to the non-homogenous nature of menses and the differing amounts of menses present to dissolve regions of the embedded therapeutic agent into, rather than out of, the tampon.

Yet another type of medicated tampon device has been reported—a dry, compressed, absorbent tampon pretreated with small quantities of bactericides or antivirals. For example, U.S. Pat. No. 5,000,749 teaches the use of iodine. However, in this and similar products, the intent is that the therapeutic agent remain within the tampon during use in order to deal with a problem that can be caused by the tampon, such as the proliferation of bacteria that occurs in the triggering of toxic shock syndrome. The iodine prevents *Staphylococcus aureus* from growing within the tampon and consequently prevents the creation and absorption of bacterial toxins by the surrounding vaginal tissue.

Other disclosed devices (e.g., U.S. Application 2001/000993A1) cover the addition of flowable therapeutic formulations to dry, compressed tampons. They are useful for postoperative management of cervical surgery. This is more complicated in that it requires the user to inject a therapeutic agent into each tampon, causing the tampon to expand. Subsequent insertion of this treated tampon into the vagina is complicated by the premature expansion of the tampon. Additionally, release of the added therapeutic agent is retarded by the absorbent nature of the compressed tampon. Dry, compressed tampons are intended to absorb and retain flowable therapeutic formulations, not to reproducibly dispense them to the surrounding vaginal tissue. For example, Pauletti in U.S. Application 2003/0049302 A1 describes the use of a conventional compressed, absorbent tampon with an attached mucoadhesive composition containing a topical vaginal or systemic cancer therapy agent. This mucoadhesive composition adheres to the vaginal tissue, facilitating the long-term absorption of the contained therapeutic agents.

Purely mechanical means of introducing flowable therapeutic formulations into the vagina require the incorporation of a rupturable sac within a tampon (U.S. Application 2003/0153864). Alternatively, this rupturing of the capsule can be initiated by body temperature melting the capsule (U.S. Application 2003/0191439). Such devices are difficult to manufacture and vary in their ability to deliver uniform therapy.

Harrison (U.S. Pat. No. 6,086,909) also discloses a tampon intended to carry a drug into the vagina with the intention that the drug be absorbed transvaginally during menstruation. The design of the tampon and the location of the embedded drug are configured to permit the absorption of menses without contaminating or interfering with the release and transvaginal absorption of the drug released from the tampon. This invention shares the limitations described above for similar devices.

Thus, there is a need for a vaginal drug delivery system and method that overcome the limitations of the prior art in a manner which results in an economical design for dispensing flowable therapeutic formulations onto the vaginal surfaces irrespective of the conditions present in the vagina.

SUMMARY OF THE INVENTION

The present invention overcomes the drawbacks of the prior art by providing a safe, reliable, inexpensive, and easy-to-use drug delivery system and method that can be utilized for the treatment of disease, for the prevention of pregnancy, and for the prevention of diseases such as HIV and other sexually transmitted diseases introduced through the vagina. In preferred embodiments, the invention's delivery system includes a soft, multilayer device charged with a flowable therapeutic formulation. This device can be inserted into the vagina, preferably by digital placement, and continuously releases a flowable therapeutic formulation through its outer surface, which is in contact with the vaginal surfaces.

In preferred embodiments, the device has low density prior to being loaded with a therapeutic formulation; it is soft; and the outer surface is wet from the contained, flowable therapeutic formulation, making the device easy to insert with minimal friction and resistance. Consequently, in its primary applications, the device can be used menstrually and intramenstrually without being affected by the dry or moist state of the vaginal tissue. The device may be easily packaged in a non-compressed state, for example, in a watertight package. Also, in preferred embodiments, the device may be disposable and biodegradable. While the preferred and less costly embodiments of the invention are insertable into the vagina by the user's finger, the device may also be designed for insertion using an inserter, such as a piston-type vaginal applicator similar to those used for tampons.

In preferred embodiments, the device of the invention includes a reservoir that serves to contain the flowable therapeutic formulation. The reservoir releases the flowable therapeutic formulation when the device is in use. The reservoir is partially or completely enveloped by a covering. The physical characteristics of the reservoir and covering are chosen to assist in driving the flowable therapeutic formulation from the reservoir, via the capillary spaces or pores of the reservoir, into and through the surrounding covering, to the outer or external surface of the device, and from there to the vaginal surfaces, as required. The flowable therapeutic formulation may be prepared using a wide variety of thickeners or other excipients, resulting in a wide variety of physical and chemical characteristics, which are known to those with expertise in the art of preparing pharmaceutical formulations.

The therapeutic agents included in the formulation may be selected from the group of hormonal and non-hormonal contraceptive agents, vaginal spermicides, vaginal microbicides, antibacterial agents, antifungal agents, antiviral agents, anti-HIV agents, anticancer agents, or combinations thereof. A tabulation of vaginal microbicides, whose use is contemplated by this new device, is contained in *Microbicide Quarterly*, Volume 2, Number 1, January through March of 2004.

With respect to the prevention of HIV and STI's, the release of a flowable therapeutic formulation into the vagina is intended to provide an active agent that will coat and/or be absorbed by vaginal tissues in order to inactivate infectious agents or prevent their access to susceptible tissues or cells.

Devices of the invention may include a securely attached withdrawal cord of suitable material, for example, textile or plastic material. The device may also include appendages affixed to the perimeter or external surface of the device to facilitate its removal. Finger pockets may also be included to facilitate insertion of the device into the vagina. The uncompressed device, charged with flowable therapeutic formulation, may be sealed in an easy-to-open, watertight package, similar to that used for packaging latex condoms.

In general, the pores within the reservoir, in the one or more layers surrounding it, and at the external surface of the covering, are such that in the absence of any external pressure, the flowable therapeutic formulation will naturally migrate towards and within the pores of the outermost-covering material. This migration is driven primarily by capillary forces resulting from interaction of the flowable therapeutic formulation with the structural surfaces of the reservoir, covering material, and the dimensions of the pores within them. The migration can be controlled by manipulating the various factors that influence capillary forces, including but not limited to (a) the dimensions of the interconnected pores in the reservoir and in the enveloping covering; (b) the contact angle between the flowable therapeutic formulation and the structural surfaces of the reservoir and cover material; and c) the viscosity and other physico-chemical characteristics of the therapeutic formulation. With the appropriate choice of materials and formulation characteristics, the flowable therapeutic formulation will spontaneously migrate to the outermost pores of the enveloping covering of the device. In doing so, the available flowable therapeutic formulation within the total device will continue to accumulate at the outermost surface of the device from which it can lubricate the device during insertion. Following insertion, the device will transfer flowable therapeutic formulation to the vaginal surfaces. As the outside surface of the device is depleted of flowable therapeutic formulation, it is replenished by the continued migration of flowable therapeutic formulation from the reservoir to the outermost pores of the enveloping covering. Additionally, and as mentioned above, the extrusion of flowable formulation may be augmented by intermittent compression of the device by variations in the physiologic forces acting on the pelvis and vagina caused by activities such as breathing, coughing, standing, walking, sitting, urinating and sexual intercourse.

In a preferred manner of carrying out the invention, the device, in a filled and surface pre-wetted, uncompressed state, does not adhere to dry, unmoistened vaginal tissue. This is a particularly desirable feature for use of the device during non-menstruating days of the menstrual cycle, in order to avoid damage to vaginal surfaces which can occur when a dry, absorbent device such as a tampon is put in contact with unmoistened vaginal tissues. As is known in the art, a dry tampon can stick to the epithelial surfaces of the vaginal walls, and cause epithelial denudation when it is removed. In its preferred embodiments, this invention avoids that danger.

It should be noted that while certain preferred embodiments of the invention, as described above, take advantage of differential capillary forces between the reservoir and covering in the delivery of a therapeutic formulation to vaginal surfaces, other embodiments of the invention may be made that rely significantly on the physiologic forces acting on the device. In this case the size of the pores or other structural features in the outer layer(s) control the speed of the flow of the therapeutic formulation from the reservoir onto vaginal surfaces. However, as taught by this invention, the design of such an embodiment would take into account the capillary forces of the materials and their interfaces, so as not to unduly inhibit or accelerate the delivery of the therapeutic formulation. In addition, it is desirable that embodiments that rely significantly on physiologic forces and resultant physical compression of the device for extrusion of the flowable formulation preferably use materials such that the capillary forces of the device components resist re-absorption of the therapeutic formulation back into the device.

The invention recognizes that there may be certain occasions where a slow release of therapeutic formulation is desired. This slow release is accomplished, in certain embodiments, by careful selection of the outer or intermediate covers. For example, the outer cover (or an intermediate cover, FIG. 34) may be composed of:
- a dense non-woven material with small pores and fiber surface characteristics which together reduce the speed of flow out of the device; or
- a partially occlusive layer such as a film with few or small apertures; or
- an outer coating designed to dissolve only in the presence of moisture and/or body heat.

Also, slow release may be obtained by designing the device so that the capillary forces that propel the flowable therapeutic formulation from the reservoir to the surface are reduced in amplitude, compared to the capillary forces that would be used for a more rapid release.

BRIEF DESCRIPTION OF THE DRAWINGS

Some of the features of the invention have been stated. Other features will appear as the description proceeds, when taken in connection with the accompanying drawings.

FIGS. 3, 4 and 5 are sectional views, similar to FIG. 2, showing alternative embodiments.

FIG. 12 depicts a device with another type of withdrawal cord.

FIGS. 13-14 illustrate a device with a simplification of the withdrawal cord attachment suited to automated device manufacture.

FIGS. 16-17, 18-20 and 21 illustrate three alternative embodiments permitting easy holding of the device during insertion and removal.

FIG. 22 is a plan view of an elongated form of the device and which can be used to surround the cervix or be positioned generally parallel to the vaginal axis.

FIG. 23 is a sectional view of the device of FIG. 22 taken at line X-X.

FIG. 24 shows the device of FIGS. 22 and 23 formed to be inserted to surround the cervix.

FIGS. 30-33 show a device with an adaptation of the constructions shown in FIGS. 1-5 and 25-29, in which similar or different reservoirs may be employed to control flowable-material release.

DETAILED DESCRIPTION OF THE INVENTION

While the present invention will be described more fully hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

As used herein, the following terms shall have the definitions set forth below:
1. A "therapeutic agent" refers to an active ingredient in a therapeutic formulation. A therapeutic agent may provide one or more medical benefits to a woman, including, but not limited to:
   a. the prevention of various diseases,
   b. the prevention of pregnancy, i.e., contraceptive effects, and
   c. the treatment of various diseases.
2. A "therapeutic formulation" is a pharmaceutical formulation that includes one or more therapeutic agents. In addition to a therapeutic agent, a therapeutic formulation may include thickening agents, lubricants, pH buffering agents and other excipients that are familiar to those skilled in the art of pharmaceutical formulations.
3. The term "flowable therapeutic formulation" refers to a therapeutic formulation that is capable of running, flowing, percolating or wicking within and between porous media and for which the liquid may consist of one or more phases, with the predominant phase being either aqueous or oily in nature.
4. "Vaginal surfaces" refers to the vaginal walls and other surfaces that would be in contact with a flowable formulation placed in the vagina. These surfaces may include the cervix, the vaginal walls, the vaginal fornices, and the vulva.
5. The term "capillary forces" or "capillary suction forces" is used to denote the forces resulting from the complex interaction of flowable materials, their surface tension, surface contact angles of wetting, and pore sizes that influence the interaction of fibrous or other similar porous materials with flowable liquids.
6. The term "physiologic forces" refers to the forces that may exert pressure on a device of this invention when the device in the vagina, including, but not limited to, differences in pelvic or vaginal pressure caused by breathing, standing, walking, sitting, urinating and sexual intercourse.

Figure 1:
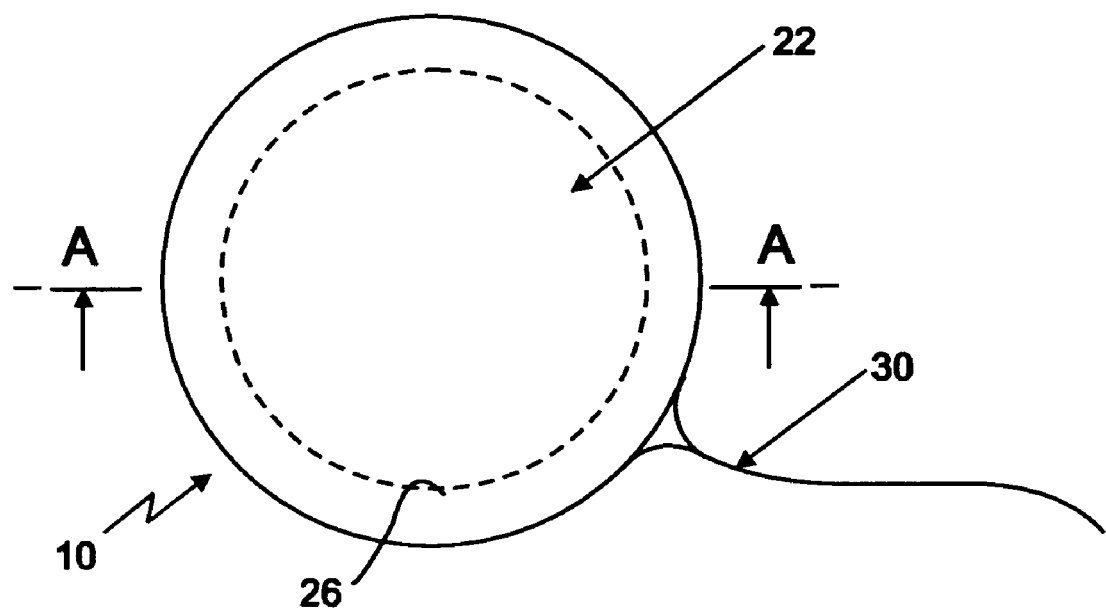
FIG. 1 is a plan view of one vaginally inserted drug delivery device of the invention. The body of the device is flat and has a symmetrical circular shape.
Figure 2:
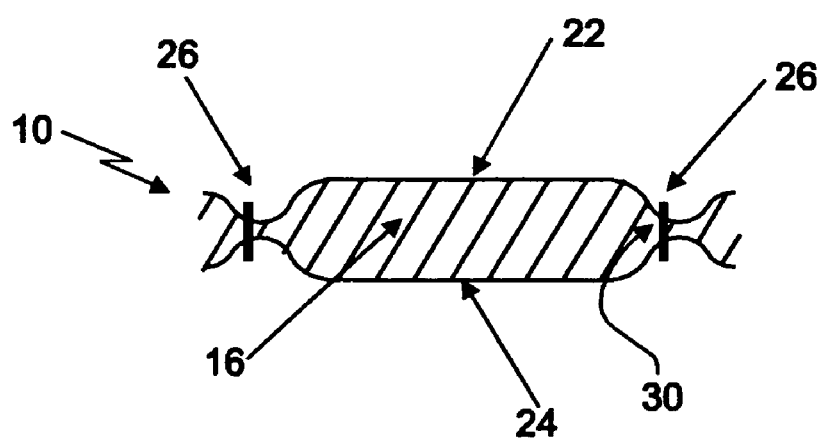
FIG. 2 is a sectional view of the device of FIG. 1, taken substantially at line A-A.

Referring to the drawings, and particularly to FIGS. 1 and 2, there is shown one embodiment of an insertable device 10 constructed in accordance with the present invention. As mentioned above, device 10 preferably is a disposable device that is charged with therapeutic agent(s) contained within a flowable therapeutic formulation and is suitable for insertion into the vaginal cavity to reside typically at or near the cervix.

Figure 6:
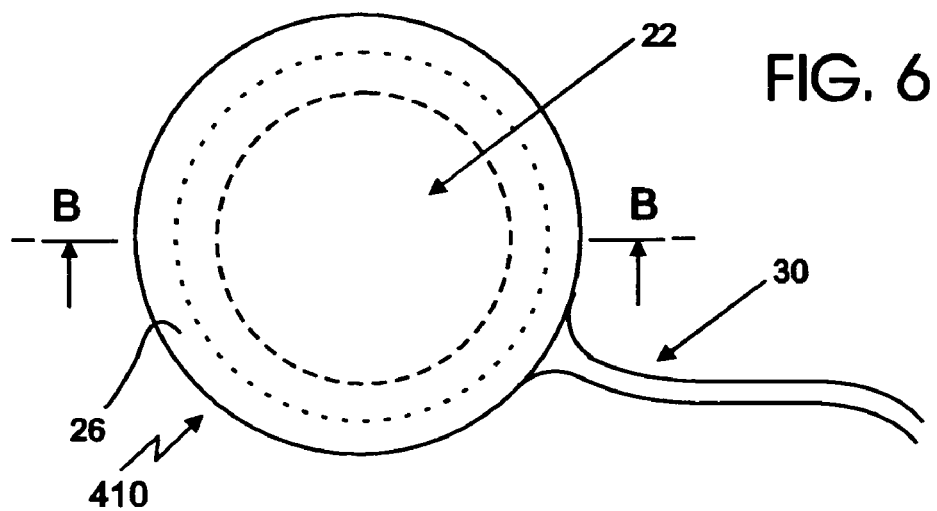
FIG. 6 is a plan view of an alternative embodiment having a free-floating reservoir.
Figure 7:
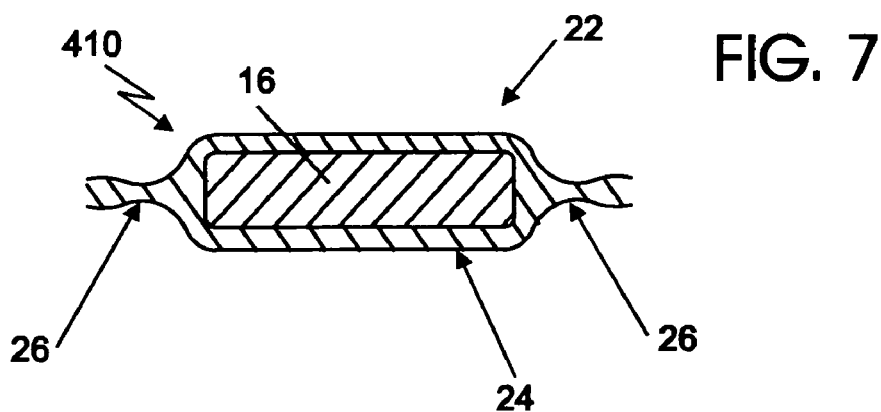
FIG. 7 is a sectional view of the device of FIG. 6, taken substantially at line B-B.

Device 10 has a flat, circular configuration and includes a reservoir 16 and an enclosing covering comprising top and bottom covers 22 and 24, respectively. The boundaries of reservoir 16 are generally coterminous with the boundaries of top and bottom covers 22 and 24. These three layers of device 10 are secured together by a circular seal 26. Seal 26 may take the form of stitching, gluing, heat sealing or other suitable form. It may extend through the three layers, as shown in FIGS. 1 and 2, or only through covers 22, 24 as shown in FIGS. 6 and 7. Seal 26 may be set inwards from, near, or coterminous with the perimeter edge. When it is desired to include a withdrawal cord as a part of device 10, for ease in manufacture the cord (for example, withdrawal cord 30, FIG. 1) may be incorporated into the device in the same operation that forms the seal.

Materials used for top and bottom covers 22, 24 may be identical, similar, or different. For example, the material of cover 22 may be permeable to the flowable therapeutic formulation and the material of cover 24 can be less or more permeable than cover 22. In other embodiments, cover 24 may be impermeable to flowable therapeutic formulation, permitting device 10 to discharge flowable therapeutic formulation through only one surface; i.e., the outside surface of cover 22.

The cross-sectional views of FIGS. 3, 4 and 5 illustrate several possibilities for device configuration and perimeter sealing. In FIG. 3, seal 26 of device 110 is achieved by a combination of heat and pressure as an intermittent or continuous seal. FIG. 4 illustrates an asymmetric shaping of device 210 to permit intimate cervical contact, using a ring-shaped reservoir 16 over-wrapped around the perimeter seal with cover 22 and sealed to cover 24 inboard of the reservoir profile 165. Referring to FIG. 5, the perimeter and the sealing of device 310 are contiguous and coterminous at 260. This configuration may be achieved by a heat or pressure sealing process.

Referring to FIGS. 6 and 7, a device 410 is shown wherein the reservoir 16 is not physically attached to the top and bottom covers 22 and 24. This free-floating reservoir 16 is in contact with the inner surfaces of covers 22 and 24 but is not secured at the seal 26 joining top 22 and bottom 24 covers. Varying the formation of the periphery of the device, by including or excluding component layers in joining cover 22 to cover 24, is one means to control the softness of the peripheral edge and the flexibility of the entire device.

Figure 8:
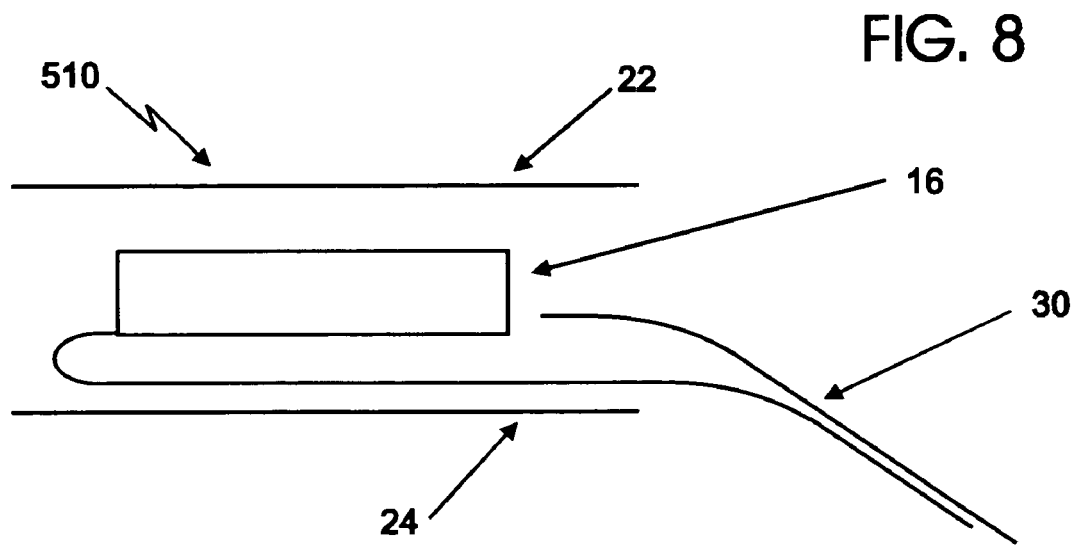
FIG. 8 is a sectional view of a further alternative embodiment incorporating a removal cord.

FIGS. 8-11 show the use of different-shaped covers 22 and 24. FIG. 8 shows a device 510 with a unique juxtaposition of covers 22 and 24 and reservoir 16, together with a withdrawal cord 30.

Figure 9:
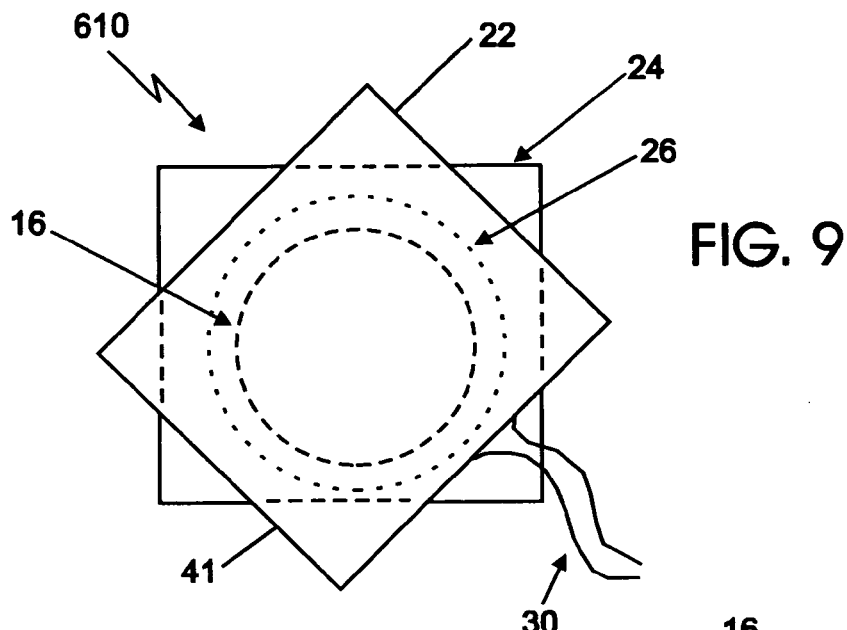
FIGS. 9-11 show, in plan, alternative embodiments with different shaped coverings for achieving various advantages, including easier grasping of the device for insertion or removal.

FIG. 9 shows a device 610 in which covers 22 and 24 are square, with one cover offset by an angle of approximately 45° relative to the other before covers 22 and 24 are sealed together to envelope the reservoir.

Figure 10:
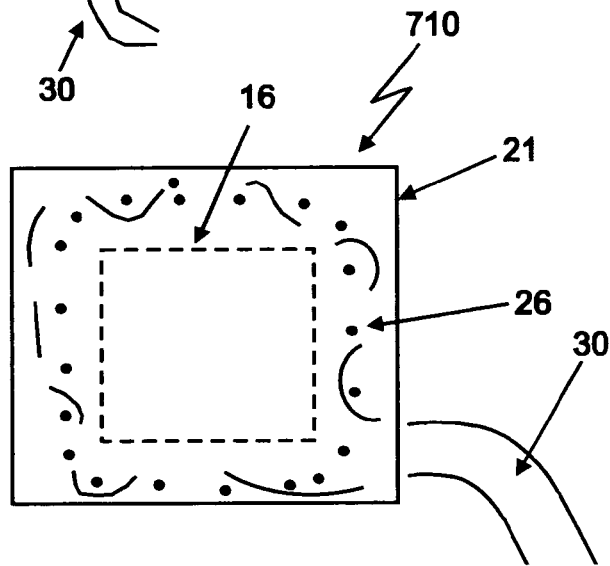

FIG. 10 shows another device 710 with square covers 22 and 24, but with essentially zero offset and with the cover perimeters coterminous.

Figure 11:
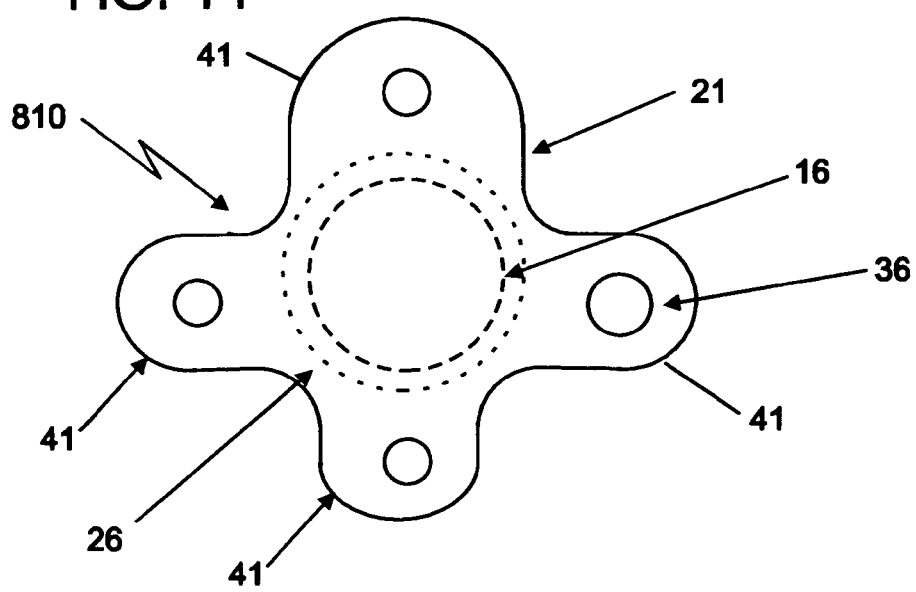

Changing the device perimeter profile, and more particularly the profile of the covers 22 and 24, can provide flexible flange extensions to the edges of the device that are suitable for grasping during insertion and removal. For example, FIG. 11 illustrates a device 810 with flexible flange extensions 41 in the form of a four-petal flower design. The user's ability to grasp the petals may be augmented by the addition of grasping holes 36 punched through the extended petal/flanges 41 of either or both covers 22 and 24. Those skilled in the art will understand that many such peripheral grasping points can be configured in the assembly of this device, and that the number of flange extensions or petals may be fewer or greater. For example, a device with three petals might have a reduced likelihood of tearing during removal by pulling on one petal, since the angle would be 120 degree rather than 90 degrees, but a device with four or five petals might be easier to remove because there are more petals to grasp.

The description above has described several ways a withdrawal cord, if required, can be attached to the device. Another attachment technique is shown in FIG. 12. Device 910 is assembled from two covers 22 and 24 and a reservoir 16, all of which are coterminous at the periphery, and about two inches in diameter in this particular example though other sizes are contemplated. The withdrawal cord 30 has been formed from a loop of cord pushed through the device at a location close to and inside the boundaries of the sealing line 26.

FIGS. 13 and 14 illustrate a device 1010 with the attachment of a single withdrawal cord 30 that has been bonded to one of the device covers 22 with a series of adhesive seals 18, using cold glue, hot melt glue, thermal or ultrasonic bonding.

Figure 15:
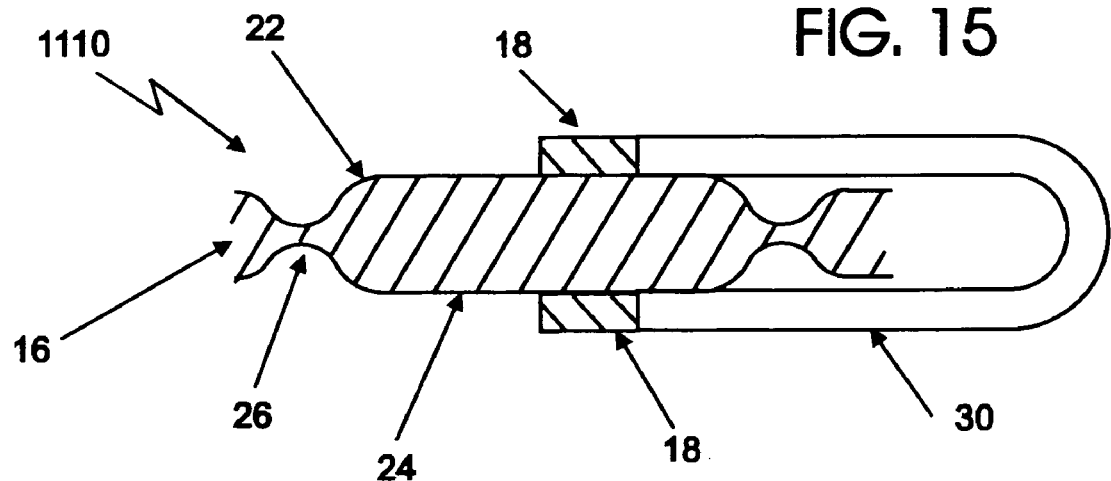
FIG. 15 illustrates another withdrawal cord attachment technique.

In another embodiment, shown in FIG. 15, the withdrawal cord 30 of device 1110 includes a single loop of cord or plastic film strip, one end of which is affixed to the surface of cover 22 with the other end affixed to the surface of cover 24 at bonding points 18.

Figure 16:
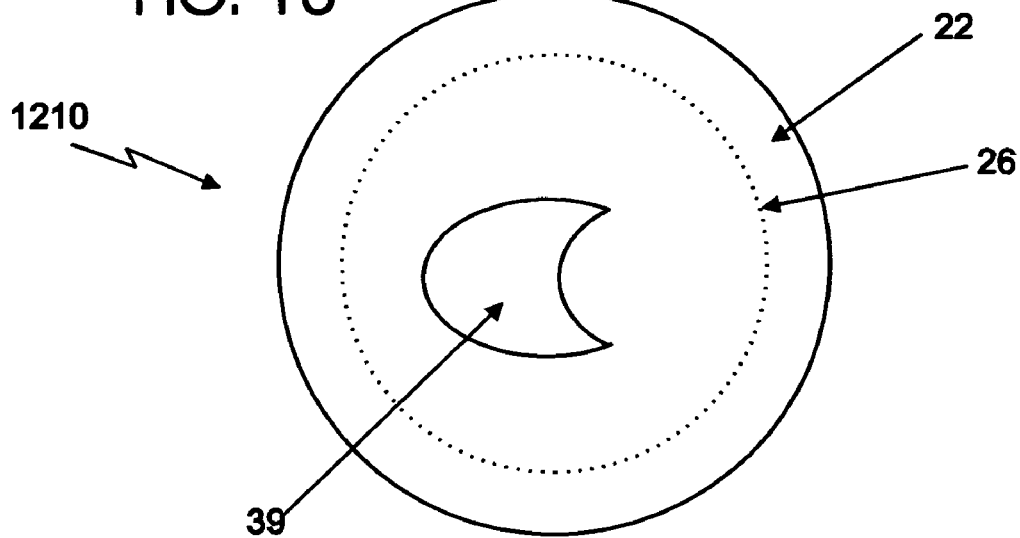
Figure 17:
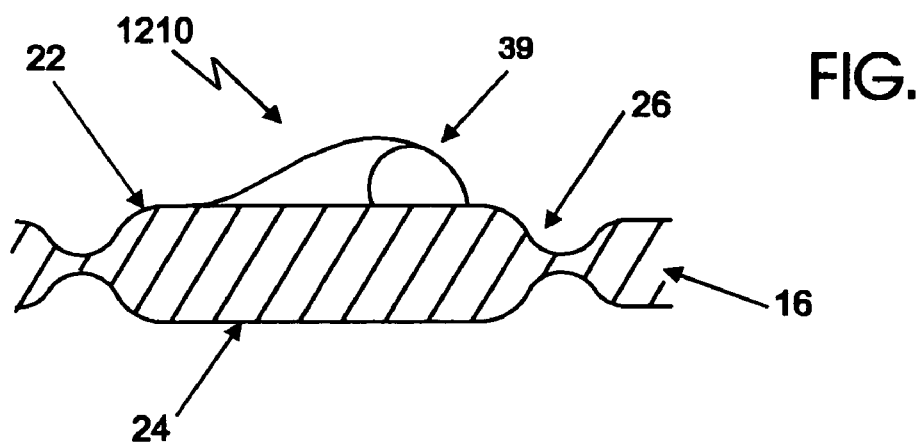

FIGS. 16 and 17 show another device 1210 that includes a finger pocket 39 attached to the top cover 22 within the sealing line 26. Finger pocket 39 permits the user to support device 1210 during insertion and to position the device at or near the cervix. It should be noted that the preferred structure of device 1210 is one where a positioning and removal feature is attached to one cover 22 leaving the other cover 24 free of obstructions and able to make intimate contact with the cervix and surrounding vaginal tissue.

Figure 18:
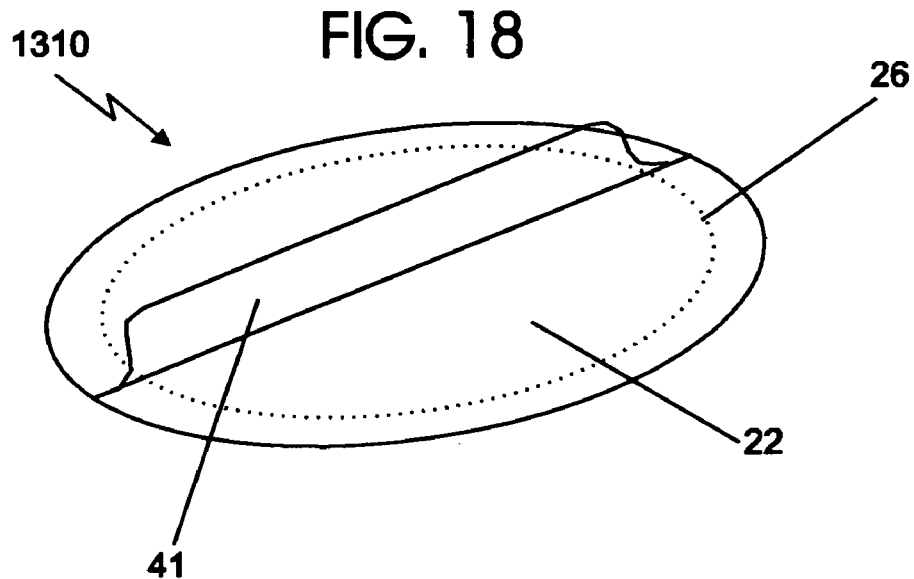
Figure 19:
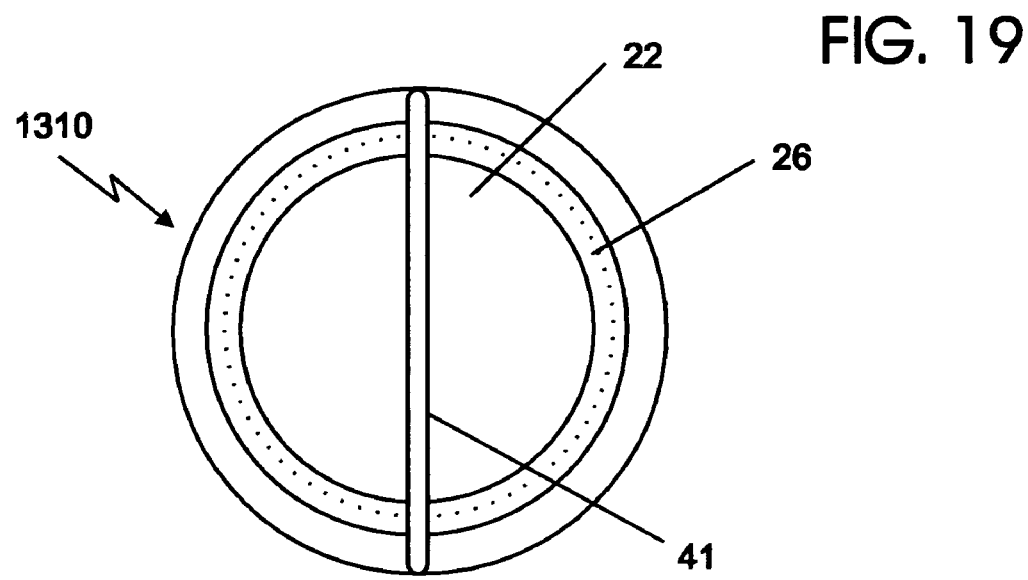
Figure 20:
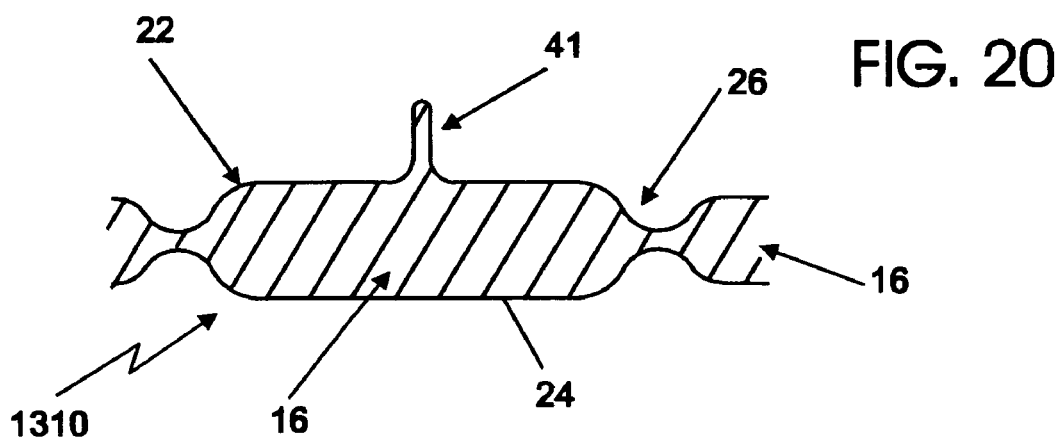

FIGS. 18, 19 and 20 illustrate another device 1310 including a grasping flange 41 that is constructed from a pleat of the material forming cover 22 before the device 10 is assembled, with a sealing line 26 joining covers 22 and 24 to envelope reservoir 16.

FIG. 21 illustrates a device 1410 with a less expensive and simpler grasping structure, in which two finger slits 40 have been created in the bottom cover 24. Slits 40 permit the user to grasp the device in a pinch grip between finger and thumb to initiate insertion, followed by a single finger engaged in one slit 40 to complete insertion and positioning.

While the embodiments discussed so far are intended for self insertion by women, there may be occasions when a physician would want to use the device to deliver a medication in a specific area of the vagina, for example after a surgical procedure. In such cases, the device may be configured to cover the length of the vagina or alternatively, may be configured to restrict dispensing of therapeutic formulation to regions surrounding the cervix, rather than covering it. FIGS. 22-24 illustrate such a device in the form of an elongated device 1510, which, for human use, may be three to four inches in length and one half to one inch in diameter. Device 1510 includes a compressible reservoir 16 that is wrapped with a covering C formed of a single sheet of material that is overlapped at 42 and sealed together. The sealing may optionally include a withdrawal cord 30 at the sealing line 26. The sealing line may be sewn through the core of the device at 26 or may simply be confined to the lower surface at the covering overlap 42. In use, elongated device 1510, charged with the requisite flowable therapeutic formulation, may be put in place and shaped by a physician or nurse during insertion to ensure dispensing of flowable therapeutic formulation to specific regions of the vagina such as around the cervix or in the fornices. In a device designed to surround the cervix, inclusion of a tensioned strip 126 of elastic material, e.g., LYCRA® material, incorporated in the overlap 42 may be used to cause the completed device to adopt the curved sausage configuration shown in FIG. 24. The embodiment shown in FIGS. 22-24 would also lend itself to self-insertion by women with the use of a cylindrical inserter device such as those typically used with tampons.

Figure 25:
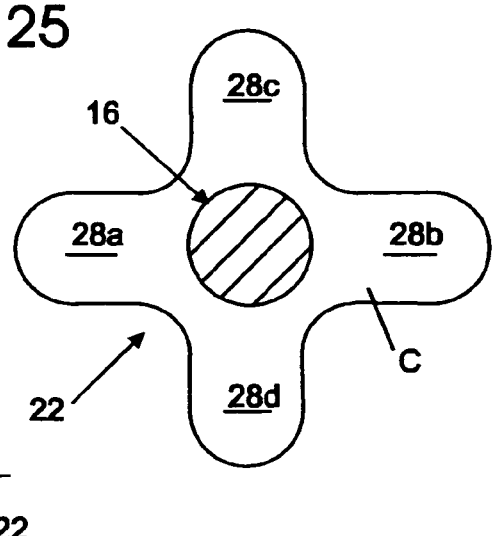
FIGS. 25-29 show an alternative form of the device construction providing an asymmetric cross-section intended to concentrate flowable therapeutic formulation release from one side of the device.
Figure 26:
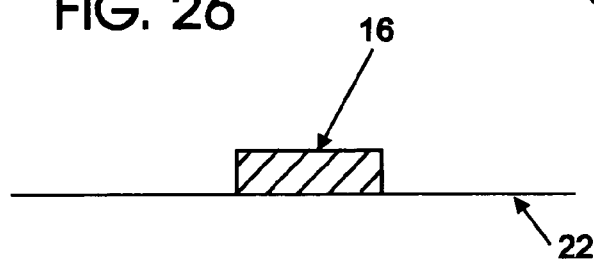
Figure 27:
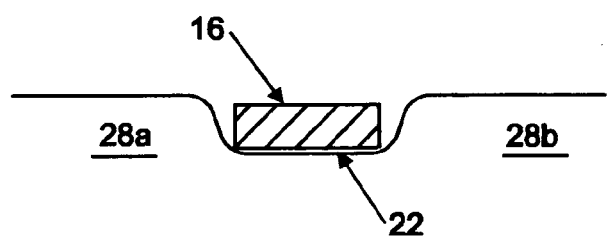
Figure 28:
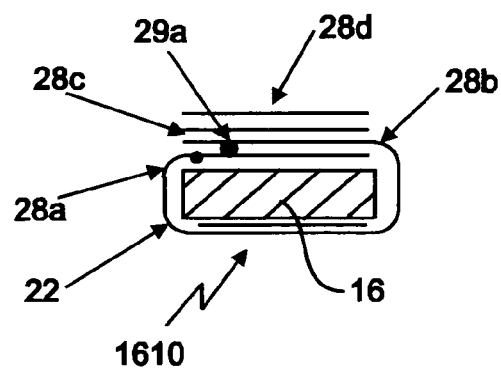
Figure 29:
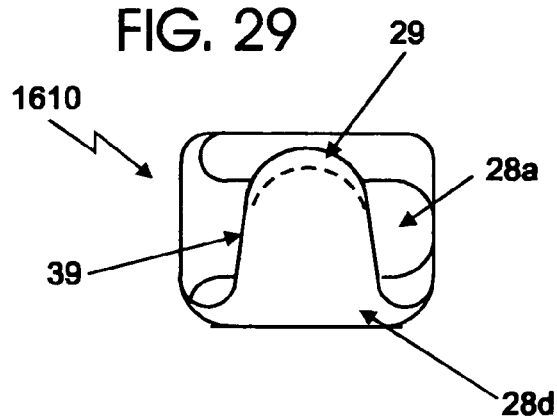

FIGS. 25-29 show a device 1610 having a covering C formed of a single sheet of material die cut to a shape such that when it is folded as shown to envelope the reservoir 16, any bulk caused by three dimensional folding is minimized. In the illustrated embodiment, a flower-shaped piece of material is die cut with four flaps 28a, 28b, 28c, and 28d (FIG. 25). The reservoir material 16 is centered on the covering C (FIG. 26), pressed into it (FIG. 27) and flaps 28a and 28b folded in sequence over the reservoir (FIGS. 28 and 29). These flaps are held in place by the folding and sealing of flaps 28c and 28d over flaps 28a and 28b. The final sealing of flaps 28c and 28d can be configured to secure all flaps over the reservoir and also create a finger pocket 39 between flaps 28c and 28d. As will be appreciated by those skilled in the art, the number of flaps may be fewer or greater than four.

FIGS. 30-33 show a device 1710 incorporating more than one reservoir into the device, in this case, two reservoirs 16a and 16b. Each reservoir may contain the same flowable therapeutic formulation and therapeutic agent, or they may contain different flowable therapeutic formulations, therapeutic agents or reservoir materials 16. The different therapeutic formulations and reservoir materials may be selected for differing release rates. Sealing the flaps 28a and 28b at 29c and the sealing of flaps 28c and 28d at 29d holds the covering over the two reservoirs.

For the embodiments shown in FIGS. 25-29 and 30-33, the size and shape of the flaps may be configured so that varying amounts of the material forming reservoirs 16 are not covered by covering C. Such a structure may be used to provide rapid release of some of the therapeutic formulation at the time of insertion, while retaining the remaining therapeutic formulation for later release. Similarly, while not illustrated, embodiments shown in FIGS. 1-24 may be formed with perforations to provide for rapid release of some of the therapeutic formulation at the time of insertion.

Figure 34:
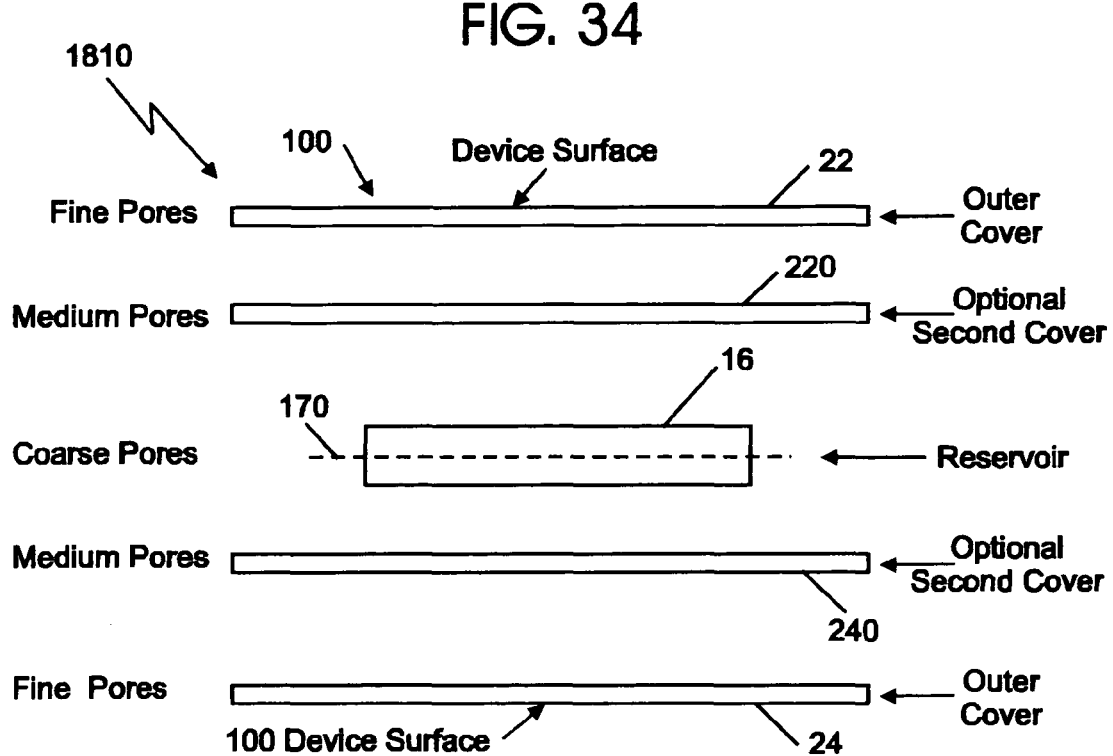
FIG. 34 is an exploded cross-section of an alternative embodiment in which additional cover layers are incorporated above and below the reservoir. The reservoir and layer structures are arranged so that there is a step change in pore size distribution and/or surface wetting characteristics as one moves from the central plane of the reservoir and towards opposite surfaces of the device.

FIG. 34 shows another device 1810 in an exploded sectional view taken along a diameter. The covering for device 1810 includes two layers on each side of reservoir 16, instead of one. Thus, device 1810 comprises two outer covers 22 and 24, two intermediate covers 220 and 240, and a reservoir 16 symmetrically or asymmetrically located about the mid-plane 170. The surface and porosity characteristics of the reservoir are such that when it is filled with a defined flowable therapeutic formulation, there are relatively low capillary forces causing the flowable therapeutic formulation to be retained by the reservoir. The surface and porosity characteristics of the materials comprising the intermediate covers 220 and 240 possess higher capillary and directional surface tension forces regarding the flowable therapeutic formulation causing it to migrate into them. The outer covers 22 and 24 have surface and porosity characteristics which create an even higher capillary and directional surface tension force on the flowable therapeutic formulation, higher than those of the intermediate cover materials and substantially greater than those of the reservoir. All other things being equal, a discontinuous gradient distribution of average pore sizes, with the reservoir 16 material having coarse pores, the intermediate cover 220, 240 materials having medium pores, and the cover materials 22, 24 having fine pores, and as shown in FIG. 34, is one way to cause flowable therapeutic formulation to migrate under the action of capillary forces from the reservoir to the outermost surface of the device at 100. By establishing a gradient of progressive change running from reservoir to each outer component surface in which the progressive change is the result of an interaction between each of the component layer structure and materials and the properties of the flowable therapeutic formulation to be contained within it, one may create a device system whereby the contained flowable therapeutic formulation is driven continuously to each component surface until it is saturated with flowable therapeutic formulation and the flow dynamics attain equilibrium. Thus, the total device illustrated in FIG. 34 utilizes discontinuous steps in driving gradient acting on the flowable therapeutic formulation as it is propelled towards each outer cover surface. The use of one or more intermediate layers may be particularly desirable if a slow release of the therapeutic formulation is desired.

Figure 35:
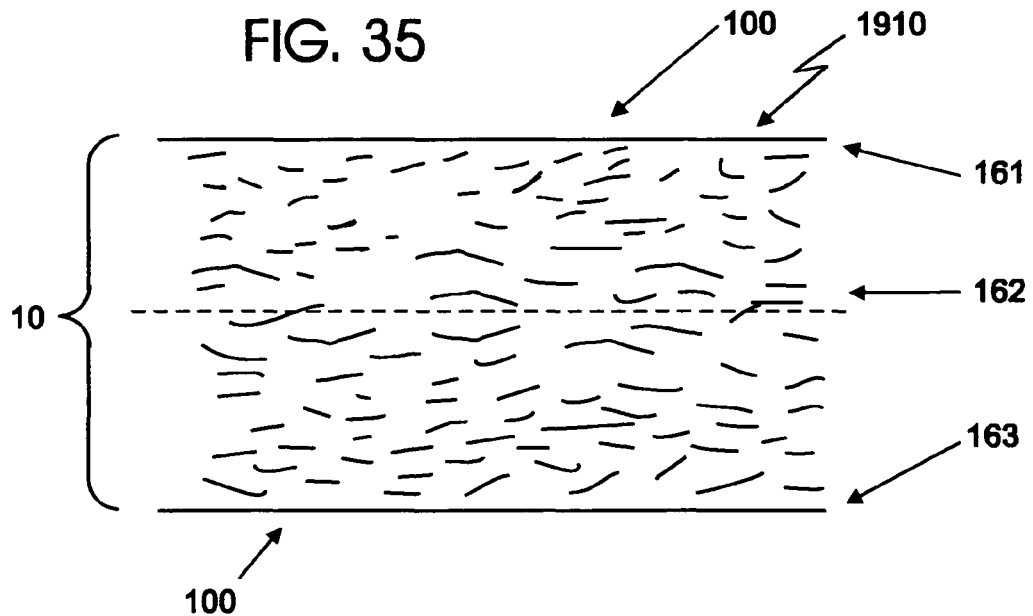
FIG. 35 is also a cross-section of an alternative embodiment in which the separately identified functional layers have been combined into a composite fibrous or foam structure having a gradient in pore size as one moves from the mid plane of the reservoir towards each face of the device.

FIG. 35 shows a cross-section of another device 1910 that incorporates a material with continuous gradients of pore structure. Rather than using different, discrete reservoir and covering materials, device 1910 uses a fibrous structure from which complete devices can be die cut. This fibrous structure may take the form of a thick mat of different fibers that are laid down in a web-forming machine capable of layering each fiber type at different horizontal planes in the total cross-section. Preferably, individual fiber layers are interblended at the interfaces between adjacent layers so that there is a smooth transition in fiber and porosity properties from one face of the mat through to the other. Fibers used in the cross-section of the composite are selected based upon their wetting and capillary behavior towards the flowable therapeutic formulation to be used. As shown in FIG. 35, the fibers at and near the approximate mid-plane 162 of the composite would define the reservoir region of the composite. These fibers have properties that permit them to hold the flowable therapeutic formulation but not resist relatively larger capillary forces tending to drain the flowable therapeutic formulation away. Moving away from the mid-plane reservoir region 162, through cover regions 161, 163, and towards each face surface 100, the type and character of fibers changes progressively causing flowable therapeutic formulation to be drawn towards each surface 100 until each surface is saturated and the flow reaches equilibrium.

Figure 36:
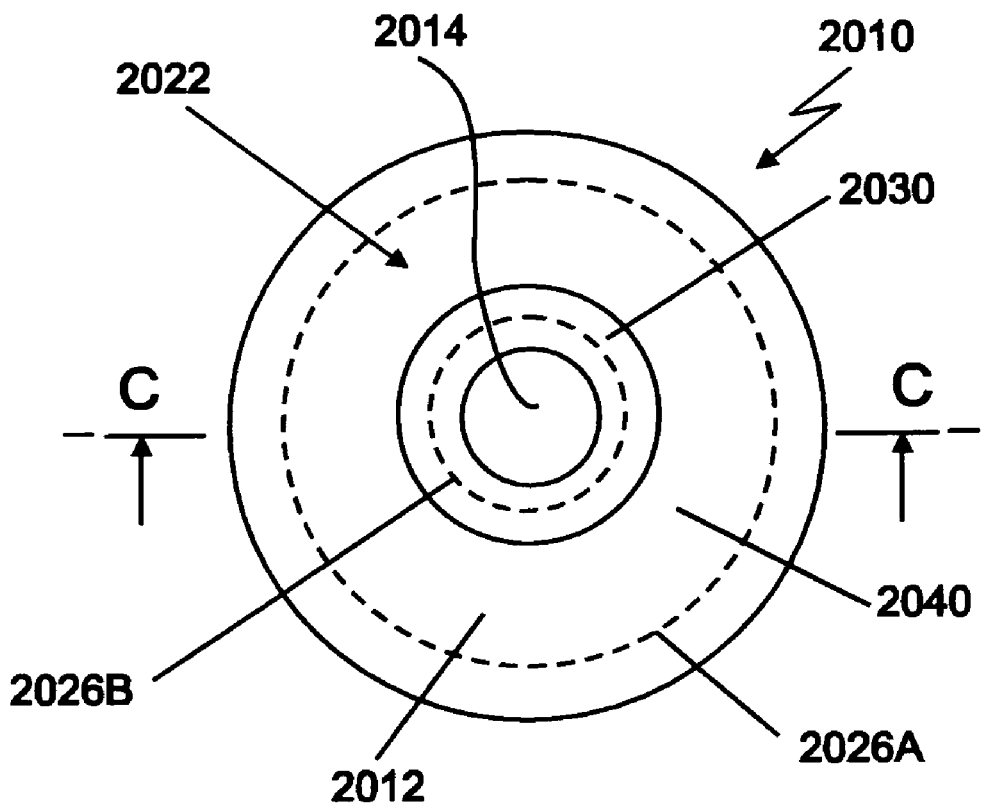
FIG. 36 is a plan view of a donut-shaped device. The donut hole can facilitate removal of the device and the shape can focus delivery of a flowable therapeutic formulation to the cervix.
Figure 37:
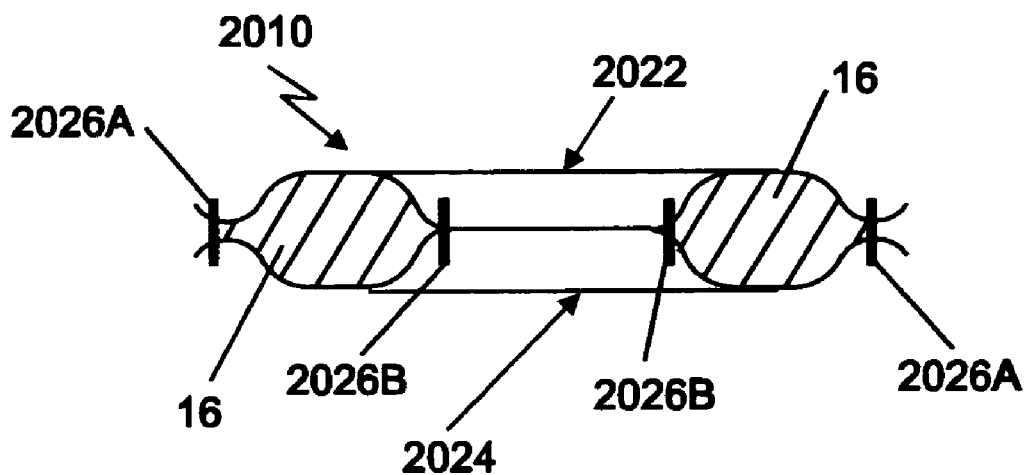
FIG. 37 is a sectional view of the device of FIG. 36, taken substantially at line C-C.

FIGS. 36 and 37 show another device 2010 that is designed to focus the release of flowable therapeutic formulation at the cervix. Device 2010, viewed in plan in FIG. 36 and in section in FIG. 37, has a relatively flat, circular donut-shape that includes a ring-shaped body portion 2012 and a central opening 2014. Device 2010 includes top and bottom covers 2022 and 2024, respectively, that envelope a ring-shaped reservoir 16. The device may be formed with circular seals at 2026A and 2026B, similar to seal 26 of the device of FIGS. 1 and 2. Device 2010 is designed for two purposes: (1) so that the hole can be easily grasped for removal; and (2) for use to surround the cervix and to provide preferential surface wetting of the device in the region that is in contact with the cervix. For the second purpose, the inward, central region 2030 of device 2010 can be designed to produce significant wetting for delivery of flowable therapeutic formulation to the cervix, while the remaining outer region 2040 is designed to produce less wetting. This focused wetting of the covering of device 2010 may be achieved by a number of means. In one embodiment, a repellent agent (not shown) may be printed on the covering material in the outer region 2040. In another embodiment, an internal baffle (not shown) may be provided in the internal structure of device 2010 to completely or partially baffle off the covering in outer region 2040 from the reservoir. These and other structures may be devised consistent with the teachings herein to achieve the focused delivery of flowable therapeutic formulation to the cervix. It will be understood that other geometries may be used to focus delivery to other areas of the vagina.

Generally speaking, and in summary, the reservoirs of the insertable devices 10-2010 described above in conjunction with FIGS. 1-37 serve as the primary storage area for the flowable therapeutic formulations that are dispersed by the devices. In this regard, the reservoir preferably is formed of a material designed to release the contained flowable therapeutic formulation from the reservoir, into and through the device covering. The covering is made from one or more layers of porous material that draw the therapeutic agent from the reservoir, maintaining the outer surfaces of the covering of the device preferentially wet. Thus, when the device is in vaginal use, typically at or near the cervix, the characteristics of the reservoir and covering materials serve to drive the therapeutic agent in a flowable therapeutic formulation to the surface of the device to thereby continuously deliver the agent to the vaginal surfaces.

Device Optimization, Including Choice of Reservoir and Covering Materials and Properties of Therapeutic Formulations, and Related Theory In the design of drug delivery devices of this invention, it is helpful to understand the primary criteria required to cause flowable liquid material to flow preferentially in one direction, and without the need for application of external pressures to all or part of the device.

Since devices of this invention incorporate porous materials, the characteristics of such materials will be explained. A porous material is one that contains internal interconnected spaces that directly or indirectly permit fluids to be stored within, or to pass through. The porosity can be characterized as the ratio of internal space to solid substance within the boundaries of the material. Alternatively, porosity can be defined by the equivalent diameters of idealized cylindrical tubes traversing the internal space of the material. Internal material voids typically are irregular in shape and character. In the case of fibrous materials, the internal material voids are usually formed by the geometrical relationship of the intersecting fibers making up the material. While an average idealized cylindrical tubular diameter can be obtained by averaging all the idealized capillary diameters within a porous material, it is more common to provide a graphical distribution of the number of idealized pores for each capillary diameter found in the material. With these data, a mean, range and modal effective pore diameter can be used to characterize the porosity of a given material.

While not wishing to be bound by theory, it is understood that liquid will move into a porous wettable medium such as a fibrous pad by capillary suction. For flowable materials with a liquid phase, the capillary suction created by the pores of the pad acting on the fluid is described by the Laplace equation $$P = \frac{2\gamma \cos\theta}{R_C}$$

Where
P=the capillary suction created.
γ=the surface tension of the liquid phase of the flowable material.
θ (Theta)=the contact angle formed between the liquid phase of the flowable material and the porous media material.
$R_C$=is the effective capillary radius of the internal pore structure of the structure.

When the capillary suction is positive, the liquid is drawn into the porous structure. When it is negative, then the porous structure is exerting a force on the fluid trying to expel the fluid from the pores.

When two fibrous or otherwise porous structures 'A' and 'B' are in contact and include the same wetting liquid contained within their own respective pore structures, no movement of liquid will occur if the capillary suction forces exerted by each structure on the contained liquid are equal. However, if there are combinational differences between contact angle, effective capillary radius for the two media in contact and containing the same fluid, then the Laplace equation allows us to predict and measure liquid partitioning between the two media. When equilibrium occurs, $$P(\text{MEDIA } A) = P(\text{MEDIA } B).$$

That is, liquid does not flow from one structure to the other. Creating an imbalance between the two structures will cause liquid to flow until the capillary suction forces exhibited by each structure are in balance. Thus, with the same fluid in 'A' and 'B', manipulating the effective capillary radius pore size distribution and contact angle for media 'A' to create a higher capillary suction than that in media 'B' will cause liquid to flow from 'B' to 'A'.

| CAPILLARY SUCTION FORCE | | |
| --- | --- | --- |
| MEDIA A | | MEDIA B |
| $\dfrac{\cos \theta}{R_{CA}}$ | > | $\dfrac{\cos \theta}{R_{CB}}$ |

Where
$R_{CA}$=Capillary radius in media 'A'.
$R_{CB}$=Capillary radius in media 'B'.

Liquid will be drawn from media 'B' into media 'A' until the capillary suction of Media 'A' equals the opposing capillary suction forces of Media 'B', and usually because all attractive pores are filled.

The capillary suction force created by media acting on a liquid is proportional to $$\frac{\cos \theta}{R_C}$$

and can be increased by making the effective capillary radius very small. It can also be increased by selecting a media such that the value of cosine theta (the wetting angle) is as large as possible, that is +1, or a wetting angle of zero between media surface and wetting liquid. Conversely, the suction force can be reduced and even made negative by selecting a porous media in which the wetting angle is between 90 degrees and 180 degrees (cosine theta therefore between 0 and −1).

Smaller effective capillary radii also serve to make the negative capillary suction forces higher when the wetting angle is between 90 and 180 degrees.

In terms of the devices disclosed herein, there are at least four combinations of capillary equation factors which may be manipulated to cause flow from the reservoir to the surface of the device, and to replenish liquid transferred from the surface of the device onto vaginal tissue.
1. If the device reservoir and device covering have identical effective capillary radii, and the liquid contact angle is below, say, 60 degrees for the covering and greater than, say, 60 degrees for the reservoir, flowable material will be forced from the reservoir to the covering whenever pore space within the covering is available.
2. If a small pore size covering and large pore size reservoir are made from the same material and have the same wetting angle below 90 degrees and preferably below 60 degrees with the flowable material, then capillary forces will move the flowable material from large pores in the reservoir to smaller pores in the covering.
3. If the reservoir and covering have identical effective capillary radii, and the liquid contact angle with the flowable material is above, say, 110 degrees for the device covering and greater than, say, 140 degrees for the reservoir, flowable material will be forced from the reservoir and into pores in the covering.
4. If a covering containing large pores surrounding a reservoir of small pores are made from the same material and have the same wetting angle above 90 degrees and preferably above 110 degrees with the flowable material, then capillary forces will move the flowable material from small pores in the reservoir to larger pores in the covering.

With the above discussion in mind, it will be appreciated that the reservoir may be configured from a variety of materials such as cellulosic and synthetic fibers and filaments, bleached rayon, cross-linked cellulose based fibers, porous foams, and super-absorbent gels, with the preferred choice being relatively coarse and stiff textile fibers, or as non-wovens and all of which preferably should be biodegradable. By relatively coarse, we mean fibers whose denier is typically in a range of about 2 to about 100 denier per filament. Because the device is subject to compressive forces in use and may be subject to compressive forces while in its package, it is desirable that the reservoir's structure be compressively resilient, sufficient to hold the internal surfaces of the enveloping covering apart and preventing excessive release of the flowable therapeutic formulation from the reservoir when the device is compressed and while in a watertight package prior to use. It is desirable to package the device with little or no air in the package in order to help minimize flow of the formulation out of the device during storage.

Reservoirs configured from fibrous structures in the form of sliver, roving, knit, knitted, woven, nonwoven, spun-bond, meltblown, thermal bonded, needled, high loft, reticulated foams, films, or similar structures are contemplated. It is important that the reservoir have sufficient internal-connected spaces within its structure to contain flowable therapeutic formulation. Furthermore, it is desirable that the reservoir's elements of structure have natural-surface finishes, as made or added intentionally, so that the reservoir can store and subsequently dispense the therapeutic agent by both capillary forces and physiologic pressures. It has been found that a suitable reservoir may be constructed from a high loft batting, one half inch thick and made from coarse denier polyester fiber, bonded with a binder adhesive and sold as TX 13, manufactured by the Carpenter Company, Taylor, Tex.

It will be understood that in certain embodiments the chemical and physical characteristics of the material forming the reservoir may be engineered to be phobic relative to the flowable therapeutic formulation in order to facilitate the release of the flowable therapeutic formulation as it migrates to the surrounding covering. Materials that are easily wetted by the flowable therapeutic formulation are generally less suitable for reservoir construction because the flowable therapeutic formulation would be attractively held within the reservoir due to capillary forces. These forces cause the therapeutic agent to want to remain within the reservoir and are increased when the total device is compressed, as is more likely to occur when the device is contained within the vagina. This phenomenon can be attributed to the capillary forces attracting the therapeutic material to the storage reservoir and increasing as the device is compressed. On compression, the pores within the storage reservoir are reduced in dimensions. Decreasing the capillary dimensions in an absorbent material where the absorbed, flowable therapeutic formulation wets the capillary surfaces causes the interfacial forces between wetting flowable therapeutic formulation and capillary surfaces to increase according to the Laplace equation, as will be appreciated by those skilled in the art. Therefore, it is generally desirable that the characteristics of the material comprising the reservoir be less retentive to the contained, flowable therapeutic formulation than the characteristics of the materials which comprise the covering surrounding the reservoir. Those skilled in the art will recognize that the result will be to facilitate the release of the flowable therapeutic formulation from the storage reservoir to the outer surface of the device covering.

Therefore, there are at least two physical mechanisms for inducing flowable therapeutic formulation to move from the reservoir to the covering by means other than compression:

1. Control of the contact angle between the flowable therapeutic formulation and the reservoir material, and control of the contact angle between the flowable therapeutic formulation and the covering material; and
2. Control of the interconnected pore sizes within the reservoir structure, and control of the interconnected pore sizes within the covering material.

Generally speaking, one would want the reservoir material to have a nominal contact angle greater than that of the covering material. Both materials could have wettable-contact angles, but with the reservoir material having a higher contact angle with the flowable therapeutic formulation than that of the covering material. Alternatively, the reservoir material could have a nominally repellant finish and a flowable-material-contact angle greater than 90 degrees. Thus the reservoir would have a degree of repellency towards the flowable therapeutic formulation while the covering material has a nominally wettable finish and a flowable-material-contact angle less than 90 degrees.

Having a phobic reservoir may impose special considerations on the package. Such a reservoir may want to express the flowable therapeutic formulation unless countered by pressure from the package and/or atmosphere. If there is air in the package, this may be exacerbated by high altitude/low pressure situations such as air freight. Thus, it may be desirable to exclude air from the package. In addition, if the internal surface of the package is strongly hydrophobic, that will reduce the amount of flowable formulation that is expressed during storage. To insure that the maximum amount of the flowable formulation is expressed after vaginal insertion of the device, the device may include wicking fibers in the reservoir to insure that pores are well drained.

Materials, and more specifically fiber surfaces, can be made hydrophobic by saturation with an adhesive non woven binder such as B.F. Goodrich Hycar 2600 X120 LRM and for which the level of hydrophobicity may be controlled by the addition of surfactants to the applied binder such as Aerosol OT. Cellulose fibers such as cotton, rayon and pulp may be made to be hydrophobic to a pre-determined degree by treatment with debonding agents such as quaternary ammonium compounds used in papermaking, by the use of fabric softener finishes or by the addition of finishes designated as repellant and hydrophobic. Such materials have very high contact angles when wet with both aqueous and oily materials and can be used to assist flow from the reservoir for therapeutic materials containing both aqueous and oleophobic components. A fiber finish sold by Omnova Performance Chemicals of Chester, S.C. USA as Sequapel AFC creates a surface finish which is both hydrophobic and oleophobic. In addition to driving flowable therapeutic formulation from the reservoir, such a finish may also prevent adsorption of expensive therapeutic materials by the reservoir material. Milder levels of phobicity can be provided on reservoir materials by using Omnova Performance Chemicals Sequasoft 69, which provides a contact angle with water of about 60 degrees.

While not limiting the materials from which the components of this device can be manufactured, it will be appreciated by those skilled in the art that fibers are a convenient starting and illustrative material from which to construct devices of this invention. Also, it is an example as to how other materials, such as porous foams, apertured films, and other macro and microporous materials might be beneficially incorporated.

For any given fiber material, there is a measurable and defined contact angle when it is wet by a flowable therapeutic formulation. Bleached cellulose fibers have a very low, essentially zero contact angle. On the other hand, polypropylene, polyethylene, and polytetrafluorethylene fibers have very high contact angles, between 90 and 180 degrees. Also, they are essentially repellent when the nature of the flowable therapeutic formulation is water-based. Polyester fibers are borderline wettable with water-based flowable therapeutic formulations with a contact angle around 90 degrees. Applying a finish to any one of these fibers which can alter the contact angle of flowable therapeutic formulation in contact with them. Applying waxy or olefinic materials to the surface of intrinsically wettable fibers, such as bleached cotton, can render the surface less hydrophilic which can be demonstrated by evidence of a higher contact angle. Conversely, an intrinsically non-wettable fiber can be made less repellent by the application of finish. It can also be made to be very wettable by the flowable therapeutic formulation (i.e., a lowering of the wetting contact angle to approach zero). For example, one phobic material that may be used with a therapeutic agent such as a water-based anti-HIV agent would be a quaternary ammonium fabric softener which imparts a mildly repellent character to a cellulose surface.

Covering layers, 22, 24, may be formed of a suitable material such as woven material, nonwoven material made from staple or from continuous filaments, fiber mats, knit materials, apertured films, porous papers, or like materials. Apertured films may be produced by laser, heat or vacuum aperturing devices and are commercially available as diaper and feminine hygiene top sheets, sold by Pantex International and by Tredegar Film Products. For coverings manufactured by textile, paper, or nonwoven processes, the preferred fibers are rayon, cotton, polyesters, biodegradable fibers, and traditional tampon fibers such as bleached cotton, bleached rayon, trilobal rayon, acetate, high and wet, modulus rayons, lycocell rayons, etc., generally having deniers at or below about 2.0 denier per filament. As discussed above, it is desirable that the covering material have a suitable pore structure, porosity, and surface character to facilitate driving the flowable therapeutic formulation containing therapeutic agent to the outside surface via capillary action.

In many applications of the invention, as discussed above, the primary mechanism that delivers the flowable therapeutic formulation from the reservoir to the outer surface of the device is the presence of capillary forces between the component layers comprising the device. Flow from the reservoir to the outer surface of the device is determined by the demand created at the device surface (i.e., by making the pore structure of the device's outer surface exercise a greater capillary force on the flowable therapeutic formulation contained within the reservoir than the forces exerted upon the flowable therapeutic formulation by the material's comprising the reservoir and attempting to retain it within the reservoir).

In the embodiments of FIGS. 1-7, the desired directional flow of flowable therapeutic material is achieved by selecting materials for the reservoir 16 such that the reservoir will be less wettable than the outer cover or covers. Thus, the material for covers 22, 24, is generally chosen to be compatible with the reservoir material and to be more wettable than the reservoir when in contact with the same flowable therapeutic formulation containing therapeutic material. More specifically, in embodiments such as those shown in FIGS. 1-7, the interconnected network of pores within the reservoir and the surrounding contact cover or covers creates a gradient of capillary forces that drives the delivery of the flowable therapeutic formulation to the outer surface of the external covering of the device. Typically, this works by the combination of relative-pore dimensions and capillarity characteristics of the materials that comprise the reservoir and cover or covers.

EXAMPLE

A device such as illustrated in FIGS. 1 and 2 is used for delivery of a water-based, thickened solution of a therapeutic agent, having a viscosity of 300 centipoises.

The reservoir of the device takes the form of an open, structured material with interconnected internal spaces ("pores"). The mean pore size diameter as determined by a porosimeter is in the range from about 100 microns to about 2000 microns, with a mean pore size in the range from about 200 to about 1500 microns being preferred. The reservoir material has a material-surface-contact angle with the flowable therapeutic formulation between about 20 degrees to about 60 degrees. The thickness of the reservoir is in the range from about one quarter inch to about one inch, with a thickness of about 3/8 inch being preferred for this Example.

A compatible covering for enveloping the above reservoir is formed of a hydroentangled and fibrillated Lyocell rayon non-woven material having a basis weight in the range from about 20 to about 60 grams per square meter; a thickness in the range from about 10 to about 40 thousandths of an inch; and a contact angle with the flowable therapeutic formulation in the range of about 0 to about 25 degrees. The mean pore size diameter of the covering material is in the range from about 20 microns to about 150 microns, with a preferred pore size diameter between about 40 microns to about 80 microns for this Example.

A suitable covering material matching the above characteristics is manufactured by DuPont as a 24 mesh spun-lace fabric, Style 8654, weighing 1.45 ounces per square yard (49 grams per square meter) and composed of 100% Lyocell fiber. Alternatively, one could use a similar DuPont non-woven fabric, Style 8423 weighing 2.30 ounces per square yard (78 grams per square meter) and composed of 70% rayon and 30% polyester fiber.

The overall diameter of the device may be about one to about three inches.

A structure as described immediately above will retain from about 3 ml to about 9 ml of flowable therapeutic formulation.

In view of the foregoing, it will be appreciated that the design parameters for the reservoir and covering materials may be dictated by several factors, including:
 1. The viscosity of the flowable therapeutic formulation;
 2. The delivery rate desired;
 3. The volume of flowable therapeutic formulation to be delivered;
 4. The intrinsic wettability of the reservoir material by the flowable therapeutic formulation;
 5. The intrinsic wettability of the covering material by the flowable therapeutic formulation;
 6. The difference in wettability between the reservoir and covering materials;
 7. The level of accumulated wetness required to be present on the external surface of the covering; and
 8. The pore size distribution in the reservoir and in the covering layer(s).

This specification offers sufficient information to enable one skilled in the art to address these design parameters to design an appropriate device for a wide range of therapeutic formulations, delivery rates, etc.

Sometimes, the selection of reservoir and cover materials may be dictated by the availability of material, material costs, manufacturing costs, the unique properties of the flowable therapeutic formulation and by manufacturing restrictions. In this regard, bleached cotton knit or woven fabrics, available in both economically deprived and prosperous regions of the globe, may be a suitable choice for the cover and would permit manufacturing by sewing machine, a ubiquitous process. Alternatively, a high speed low cost manufacturing plant, which would require a significant initial investment, may require the availability of covering and reservoir materials which can be heat sealed and die cut at speed. Suitable heat sealable covering materials include those which are biodegradable, have low contact angles with water, and which wet and store water-based fluids, and are available as tea bag material, manufactured in various weights and porosities by, for example, Ahlstrom Corporation, Fiber Composites Division, Windsor Locks, Conn. USA. Such products are generally available for use with different and adjustable types of heat sealing resins.

Reservoirs, as previously mentioned, may be created from structures that are thermoplastic such that the application of heat and pressure will create a perimeter seal. Thermoplastic materials in fiber or other porous form such as polyester, polypropylene, polyurethane and polyethylene resins and blends thereof may be used to create reservoirs with this kind of perimeter seal, as can many reticulated foams or interconnected fibers. Additionally, polyvinyl acetal foams, already used in medical absorbency products, may be modified in mean cell pore size and surface wetting characteristics to create a suitable reservoir.

For a high viscosity flowable therapeutic formulation, the reservoir and covering materials may be engineered so that they both have relatively large pore dimensions and that the wettability (as measured by surface contact angle) differences between the reservoir and the covering are sufficient to facilitate release of the formulation. Where a higher delivery rate is desired, the reservoir and covering materials may be engineered so that the covering material has zero or a very low contact angle and small pore dimensions.

Where it is necessary to deliver higher total volumes of the therapeutic agent, the reservoir and covering materials may generally be engineered so that the reservoir has a flowable therapeutic formulation holding capacity of about 3 grams to about 30 grams of fluid per gram of material, and the covering has a flowable therapeutic formulation holding capacity of about 2 grams to about 5 grams of fluid per gram of material. In a fibrous reservoir, the void volume can be maintained by the use of a proportion of bicomponent heat bonding fibers which, when heated in situ, create stable and somewhat compression resistant pores.

The nature of the therapeutic formulation may take the form of a simple gel similar to KY jelly, a flowable phase agent, a semi-solid material, a breakable emulsion, a rheopectic gel, or other suitable flowable form which can be contained within the structure of the reservoir and driven to the outside surface of the covering as described herein. As discussed elsewhere herein, the therapeutic agents in the therapeutic formulation may be contraceptives, antibacterials, antifungals, antivirals, anti-HIV agents, or other prophylactic or therapeutic substances.

As discussed above, the external surface characteristics of the insertable device are designed for ease of insertion and comfort of the user, particularly with respect to prewetting of the surface of the device prior to insertion. In this regard, it has been found that the covering of the device can be symmetrical about the reservoir or it may be asymmetrical. For an asymmetrical covering, the outer material on the cervical side may be chosen to be easily wet and/or non-abrasive and easy to insert with a finger, i.e., no need for traditional piston-type applicators that are used with most tampons. Where desired, a lubricating agent may be utilized to facilitate insertion. Lubricating agents for mucosal surfaces are well known to those skilled in the art, and include but are not limited to glycerin, propylene glycol, dimethicone copolyol, and various mixtures thereof.

It will also be appreciated that use of the present invention, due to the pre-wetted nature of the outside surface of the device, may aid in application of the therapeutic agent to non-cervical areas such as the vaginal walls, vulva and labia, during insertion.

While the therapeutic agent is generally applied directly to the reservoir of the device, some pretreatment of layers can be used to aid in later dispersion of the agent. These pretreatment agents, while not limited to the following, may include prewetting the reservoir fibers using de-ionized water so that more of the therapeutic agent can be physically free and only held in by the pore structure of the reservoir. Further, the reservoir may have outer layers that are biofilms designed so that the environment of the vagina decomposes these films, and the active agent is dispersed immediately or on a timed or sustained release schedule.

Test Data

A standard flowable therapeutic formulation was used to measure the migration of an agent, in this case sodium chloride, in a gel placed within the device reservoir, through the covering, and into deionized water. A series of circular devices were constructed by sewing a woven bleached cotton fabric covering around a high loft polyester fiberfill reservoir. The reservoir material for this prototype device was 100% new polyester material, high-loft batting, ½ inch thick, TX 13, made by Carpenter Company, Tyler, Tex. A formulation of 0.9% sodium chloride in KY Jelly (Personal Products Company, Skillman, N.J.), containing purified water, glycerin, hydroxyethylcellulose, chlorhexidine gluconate, gluconolactone, methylparaben, was prepared. In addition to simple addition of sodium chloride to KY Jelly, two less viscous formulations were prepared by diluting the KY Jelly 1 to 1 and 1 to 3 with purified water. These thickened flowable formulations were injected into the device reservoir. It should be noted that this standard flowable formulation can be adjusted in viscosity by the type and quantity of the thickener, and adjusted in its contact angle with a material surface by the addition of surfactants such as Tween 20.

Preliminary work on agent migration characteristics were determined by positioning each device 10 centimeters below the surface of deionized water at 37° C. in an agitated water bath. This water bath testing was done using standard pharmaceutical equipment for measuring dissolution and release of agents from a pharmaceutical formulation. Details on the test methods and equipment specifications are found in USP 28, section 711, "Dissolution."

Migration of saline from the device was measured by monitoring the increase in conductivity of the bath. Data shown in FIG. 38 suggests that the release of sodium chloride from the device is influenced by the viscosity of the formulation. With the marketed K-Y jelly formulation, about 37% of the sodium chloride was released in about 20 minutes, and 90% was released by three hours. With lower viscosity formulations, initial release was more rapid, with release of about 50% to 60% of the sodium chloride within 20 minutes.

In a second experiment, using a basket dissolution apparatus (USP 28, section 711, "Dissolution") in order to contain a simple gel formulation, the diffusion of sodium chloride from KY Jelly, was compared with its diffusion from 100% KY Jelly and a 25% KY Jelly formulation, both contained within the same device described above in connection with FIG. 38. Data shown in FIG. 39 suggests that sodium chloride diffusion from the 100% KY Jelly 100% within the device was slightly slower than from the KY Jelly without a device, but that diffusion from the 25% KY Jelly within the device was more rapid than from the plain KY Jelly. Specifically, at about 100 minutes, the estimated release using the basket apparatus was about 46% from the plain KY Jelly; about 43% from KY Jelly within the device; and about 62% from 25% KY Jelly formulation within the device.

Figure 38:
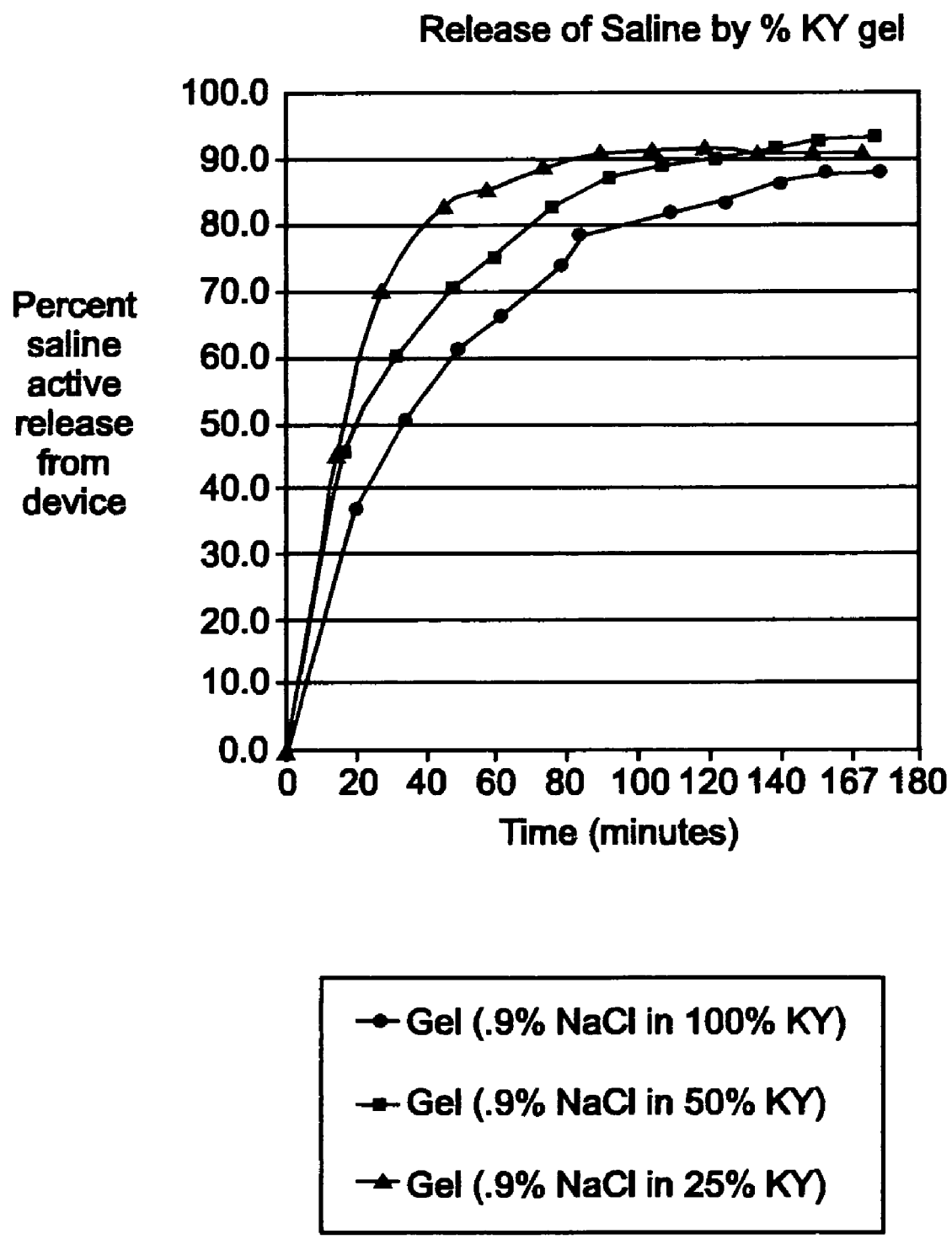
FIG. 38 is a graph showing the speed of release of sodium chloride from a test device, by differing concentrations of a gelling agent in the formulation, using a USP standard water bath dissolution apparatus.
Figure 39:
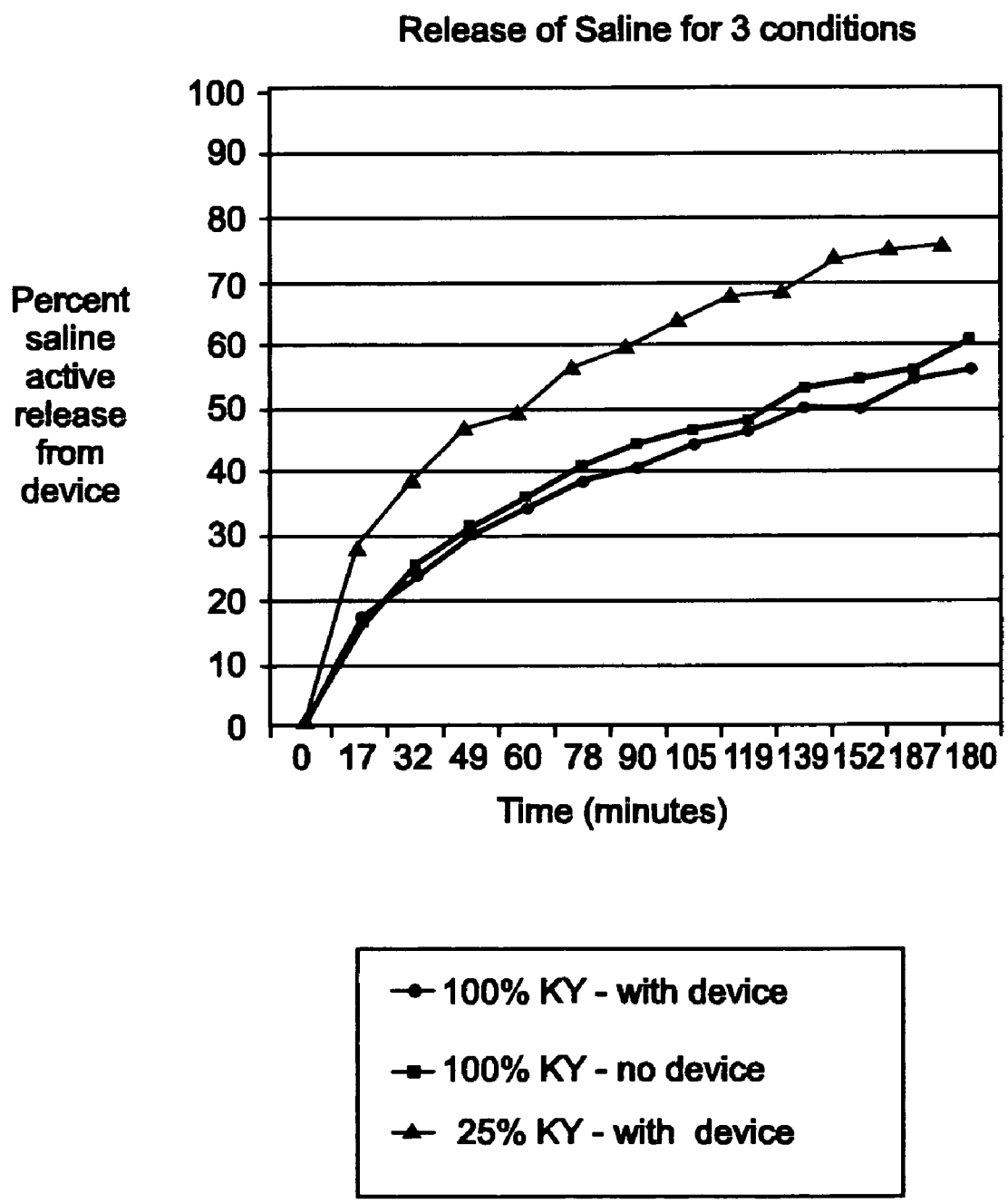
FIG. 39 is a graph comparing the release of sodium chloride from a simple gel compared with its release from a similar but less concentrated gel in a test device, using a USP standard water bath dissolution apparatus.

The data shown in FIGS. 38 and 39, being preliminary investigations on the dissolution characteristics of prototype devices, are to serve the first steps towards developing methods which could be used to evaluate the dissolution of various flowable therapeutic materials from the device.

Typical flowable therapeutic material examples suitable for this device are as follows, but by no means limiting.

Representative Anti HIV Flowable Therapeutic Formulation Compositions

Several microbicides under investigation are aqueous hydroxyethylcellulose gels, containing various additives and/or preservatives, where the active ingredient is tenofovir or TMC-120. Other anti HIV agents currently being investigated are aqueous gels based on polyacrylic acid (acidic character is the active ingredient), natural and synthetic polyanions, and surfactants, where each gel contains various additives and/or preservatives.

Other antiviral agents currently under investigation may be used in place of Tenofovir, for example Cyanovirin, Porphyrins, C85FL, and Doxovir. Alternative thickeners such as Carboset 934 and Carbopol 940 are suitable A more advanced formulation, which comprises polyethylene glycol with a Carbopol thickener, has been shown to absorb moisture from vaginal tissue over which it has spread, causing a local increase in viscosity of the flowable therapeutic formulation and increasing its adherence to vaginal tissue.

Representative Antifungal Formulation: The addition of therapeutic agents such as of 1% Tioconazole, or 1% Butaconazole, or 1% Flucanazole to a standard flowable-material formulation provides a device able to disperse antifungal material to vaginal tissue.

Representative Spermicidal Formulation: As an example, the addition of 0.95% nonoxynol-9 to the anti-HIV flowable therapeutic formulation given above in place of the Tenofovir yields a flowable therapeutic formulation which will dispense from the device and provide spermicidal properties to the vaginal fluids.

Device Insertion: As mentioned above, digital insertion of the device may be facilitated through the use of one or more finger pockets or cut openings, such as pocket 39 illustrated in FIG. 16 or the slits illustrated in FIG. 21. The pocket may have several variations, including being integral with the outer material of the covering layer. The pocket may also be incorporated within the package itself. Further, the pocket may be constructed by the user through use of an adhesive tab/backing imparted to the carrier or package. Such a pocket, while designated a finger pocket, may be used with a number of inserter devices instead of a finger. Such devices may be made from molded plastic, stick-type devices or hooks, to paper, rubber or ceramic type of inserters that would be designed to allow the user to place the device in the vagina without causing injury to the vaginal wall. The shape of the inserter, preferably, is such that the user will be able to position it for optimal placement of the device and therapeutic agent. The terms "digit" and "digital," as used herein, refer to a woman's fingers or to other means for inserting the carrier within the vagina through the use of an insertion device; for example, the curved plastic stick referred to above would act as a digit.

Also as noted previously, the device could be inserted using an inserter device similar or identical to commonly used piston-type cylindrical inserters that are used for tampons. However, while tampons are generally compressed within a cylindrical inserter device, and tampons expand substantially upon wetting, this invention is pre-wetted and would preferably be packaged in a fully wetted state, with minimal or no compression within the inserter device.

Device Removal: Devices of this invention preferably include a removal cord or tape, longer than the cord associated with a typical tampon. The longer cord is used to prevent displacement or loss of the cord in the vagina during sexual intercourse. In certain embodiments, the cord may be placed between the outer layers of the device and bonded to the reservoir in a sealing process that is known to those skilled in the art. As discussed above, devices of the invention may also be formed without a removal cord.

Device Optimization

For the development of the device with a particular therapeutic agent, several features of the design, such as fiber type or fiber derivatization, can be optimized to assure efficient vaginal delivery and to ensure that the therapeutic agent is compatible with the device, such that no adsorption onto the device occurs. The key mechanisms utilized to deliver a therapeutic agent such as a microbicide from the device into the vagina are 1) movement of the gel driven by the relatively hydrophobic core and the attraction of the relatively hydrophilic outer layer and 2) diffusion of the active ingredient.

For low molecular weight, water-soluble agents, both mechanisms, i.e. gel movement and diffusion, will serve to deliver the agent. Since low-cost bleached cellulosic fibers are commonly hydrophilic, the development of a hydrophobic inner core composed of cellulosic fiber can be done by chemically modifying the fiber surfaces, or by using unscoured washed cotton.

As the molecular size of the active ingredient increases, gel movement out of the device will be more important with regard to delivery. If the therapeutic agent is hydrophobic, which could potentially cause the agent to adsorb onto the fiber surfaces of a relatively hydrophobic core, the degree of hydrophobicity or oleophobicity of the core and outer layer can be readily adjusted by the use of various fiber coating processes known to those skilled in the art. Thus the level of core hydrophobicity may be altered to promote delivery. The level of hydrophobicity or oleophobicity of the materials used in the device may be characterized with contact angle measurements (1), water repellency tests (2), or by various infrared spectroscopy techniques (3).

(1) Castellan, G. W., "Physical Chemistry," Benjamin/Cummings, Menlo Park, 1983.
(2) AATCC, Technical Manual of the American Association of Textile Chemists and Colorists, Vol 70, 1995.
(3) Skoog, D. A., Leary, James J. "Principles of Instrumental Analysis," Saunders College, Fort Worth, 1992.

While the present invention has been described in connection with certain illustrated embodiments, it will be appreciated that modifications may be made without departing from the true spirit and scope of the invention.

What is claimed is:

1. A device for insertion into the vagina to deliver a flowable therapeutic formulation to the vaginal surfaces, said device comprising:
    a reservoir having at least one substantially planar surface;
    a flowable therapeutic formulation contained throughout the device;
    wherein said entire device is substantially phobic relative to the flowable therapeutic formulation;
    a gradation of capillary forces between the reservoir and external surfaces of the device to cause a desorption of the flowable therapeutic formulation from the device when placed in the vagina, the gradation of capillary forces formed by one of:
    (1) the reservoir and the external surfaces of the device having the same effective capillary radii, a liquid contact angle of less than 60 degrees for the external surfaces of the device, and greater than 60 degrees for the reservoir;
    (2) the reservoir having a larger pore size than the external surfaces of the device, and the liquid contact angle of the reservoir and the external surfaces of the device are less than 90 degrees;
    (3) the external surfaces of the device having a larger pore size than the reservoir, and a liquid contact angle of the reservoir and the external surfaces of the device are greater than 90 degrees; and
    (4) the reservoir and the external surfaces of the device having the same effective capillary radii, and the liquid contact angle is greater than 110 degrees for the external surfaces and greater than 140 degrees for the reservoir.

2. The device of claim 1 wherein the flowable therapeutic formulation contains a therapeutic agent that is selected from the group consisting of hormonal and non-hormonal contraceptive agents, vaginal spermicides, vaginal microbicides, antibacterial agents, antifungal agents, antiviral agents, anti-HW agents and anticancer agents, or combinations thereof.

3. The device of claim 1 wherein the flowable therapeutic formulation contains an agent selected from the group consisting of a soluble or dispersible flowable material, a flowable phase agent, and a semi-solid agent, or combinations thereof.

4. The device of claim 1 wherein the flowable therapeutic formulation comprises a soluble or dispersible flowable material in dry form which is activatable by the user by adding a liquid selected from the group consisting of water, vinegar and mineral oil before insertion into the vagina.

5. The device of claim 1 wherein the reservoir is formed of uncompressed fibrous textile material comprising relatively coarse and stiff textile fibers.

6. The device of claim 1 wherein the reservoir comprises textile fibers whose denier is in the range from about 2 to about 100 denier per filament.

7. The device of claim 1 wherein the reservoir comprises a fibrous structure selected from the group consisting of sliver, roving, knit, knitted, woven, non-woven, spun-bond, melt-blown, thermal bonded, needled, and high loft.

8. The device of claim 1 wherein the reservoir is formed of uncompressed fibrous textile material having a mean pore size diameter in the range from about 100 microns to about 2000 microns.

9. The device of claim 1, further comprising a covering formed from a material selected from the group consisted of woven material, non-woven material made from staple or continuous filaments, fiber mats, knit materials, apertured films and porous papers.

10. The device of claim 1 including a finger pocket.

11. The device of claim 1 wherein the contact angle between the flowable therapeutic formulation and material forming the reservoir is less than 180 degrees.

12. The device of claim 1 packaged in a pre-wetted uncompressed state.

13. The device of claim 1 wherein the device contains in the range from about 3 ml to about 9 ml of flowable therapeutic formulation.

* * * * *